(12) United States Patent
Vermeiren et al.

(10) Patent No.: US 9,260,355 B2
(45) Date of Patent: *Feb. 16, 2016

(54) PRODUCTION OF PROPYLENE VIA SIMULTANEOUS DEHYDRATION AND SKELETAL ISOMERISATION OF ISOBUTANOL ON ACID CATALYSTS FOLLOWED BY METATHESIS

(75) Inventors: Walter Vermeiren, Houthalen (BE); Cindy Adam, Wierde (BE); Delphine Minoux, Nivelles (BE)

(73) Assignee: TOTAL RESEARCH & TECHNOLOGY FELUY, Seneffe (Feluy) (BE)

( * ) Notice: Subject to any disclaimer, the term of this patent is extended or adjusted under 35 U.S.C. 154(b) by 103 days.

This patent is subject to a terminal disclaimer.

(21) Appl. No.: 13/583,990
(22) PCT Filed: Mar. 15, 2011
(86) PCT No.: PCT/EP2011/053905
§ 371 (c)(1),
(2), (4) Date: Oct. 8, 2012
(87) PCT Pub. No.: WO2011/113836
PCT Pub. Date: Sep. 22, 2011

(65) Prior Publication Data
US 2013/0245348 A1  Sep. 19, 2013

(30) Foreign Application Priority Data

| Mar. 15, 2010 | (EP) | .................................. | 10156537 |
| Apr. 9, 2010 | (EP) | .................................. | 10159461 |
| Apr. 9, 2010 | (EP) | .................................. | 10159463 |
| Apr. 23, 2010 | (EP) | .................................. | 10160840 |
| Apr. 27, 2010 | (EP) | .................................. | 10161125 |

(51) Int. Cl.
*C07C 1/24* (2006.01)
*C07C 5/25* (2006.01)
(Continued)

(52) U.S. Cl.
CPC .................. *C07C 1/24* (2013.01); *C07C 5/2506* (2013.01); *C07C 5/2708* (2013.01); *C07C 6/04* (2013.01);
(Continued)

(58) Field of Classification Search
USPC .......... 585/324, 327, 329, 643–647, 639, 640, 585/671, 664
See application file for complete search history.

(56) References Cited

U.S. PATENT DOCUMENTS

| 3,365,513 A | 1/1968 | Heckelsberg |
| 3,526,676 A | 9/1970 | Turner et al. |

(Continued)

FOREIGN PATENT DOCUMENTS

| DE | 890953 C | 10/1953 |
| EP | 0304515 A1 | 8/1987 |

(Continued)

OTHER PUBLICATIONS

Zhang et al. One Step Dehydration and Isomerization of n-butanol to Isobutene over Zeolite Catalysts. Chem Commun., 2010, 46, 4088-4090.*

(Continued)

*Primary Examiner* — In Suk Bullock
*Assistant Examiner* — Sharon Pregler
(74) *Attorney, Agent, or Firm* — Albert Shung

(57) ABSTRACT

A process for production of propylene can include simultaneously subjecting isobutanol to dehydration and skeletal isomerization to make a mixture of n-butenes and iso-butene. The n-butenes can be subjected to methathesis. The process can include introducing isobutanol into a dehydration/isomerization reactor and contacting the isobutanol with a catalyst at conditions effective to dehydrate and skeletal isomerase the isobutanol to make a mixture of n-butenes and iso-butene. A mixture of n-butenes and iso-butene can be recovered and fractionated to produce an n-butenes stream. The n-butenes stream can be sent to a methathesis reactor and contacted with a catalyst at conditions effective to produce propylene. A stream can be recovered from the methathesis reactor that includes propylene, unreacted n-butenes, heavies, and optionally unreacted ethylene. The stream can be fractionated to recover propylene, and the unreacted n-butenes and unreacted ethylene can optionally be recycled to the methathesis reactor.

28 Claims, 5 Drawing Sheets

(51) Int. Cl.
*C07C 5/27* (2006.01)
*C07C 6/04* (2006.01)
*C07C 7/148* (2006.01)
*C07C 7/177* (2006.01)

(52) U.S. Cl.
CPC ......... *C07C 7/14866* (2013.01); *C07C 7/14891* (2013.01); *C07C 7/177* (2013.01); C07C 2521/04 (2013.01); C07C 2521/08 (2013.01); C07C 2523/28 (2013.01); C07C 2523/30 (2013.01); C07C 2523/36 (2013.01); C07C 2523/75 (2013.01); C07C 2529/40 (2013.01); C07C 2529/70 (2013.01)

(56) References Cited

U.S. PATENT DOCUMENTS

| | | | |
|---|---|---|---|
| 3,658,927 | A | 4/1972 | Crain et al. |
| 4,469,911 | A | 9/1984 | Manning |
| 4,568,788 | A | 2/1986 | Kukes et al. |
| 4,575,575 | A | 3/1986 | Drake et al. |
| 4,684,760 | A | 8/1987 | Drake |
| 4,754,098 | A | 6/1988 | Drake |
| 4,795,734 | A | 1/1989 | Chauvin et al. |
| 5,449,852 | A | 9/1995 | Chauvin et al. |
| 5,877,372 | A | 3/1999 | Evans et al. |
| 5,895,830 | A | 4/1999 | Stine et al. |
| 5,898,092 | A | 4/1999 | Commereuc |
| 6,159,433 | A | 12/2000 | Chodorge et al. |
| 6,207,115 | B1* | 3/2001 | Chodorge et al. ............ 422/134 |
| 6,495,732 | B1 | 12/2002 | Hearn et al. |
| 6,616,910 | B2* | 9/2003 | Rouleau et al. ............... 423/706 |
| 6,686,510 | B2 | 2/2004 | Commereuc et al. |
| 6,689,927 | B1 | 2/2004 | Frame et al. |
| 6,768,035 | B2* | 7/2004 | O'Rear et al. ................ 585/331 |
| 6,777,582 | B2* | 8/2004 | Gartside et al. .............. 585/324 |
| 6,977,318 | B2 | 12/2005 | Bridges |
| 7,220,886 | B2 | 5/2007 | Podrebarac et al. |
| 7,473,812 | B2 | 1/2009 | Peters et al. |
| 2008/0132741 | A1 | 6/2008 | D'Amore et al. |
| 2008/0261230 | A1 | 10/2008 | Liao et al. |
| 2008/0312481 | A1* | 12/2008 | Leyshon ....................... 585/324 |
| 2010/0063339 | A1* | 3/2010 | Takai et al. ................... 585/646 |

FOREIGN PATENT DOCUMENTS

| | | |
|---|---|---|
| EP | 2090561 A1 | 8/2009 |
| EP | 2108634 A1 | 10/2009 |
| FR | 2608595 A1 | 6/1988 |
| JP | 2008-519033 A | 6/2008 |
| WO | 9703932 A1 | 2/1997 |
| WO | 2006052688 A2 | 5/2006 |
| WO | WO 2008136280 A1 * | 11/2008 |
| WO | 2009079213 A2 | 6/2009 |
| WO | 2009/098262 A1 | 8/2009 |

OTHER PUBLICATIONS

Vendelin Macho, et al.; "Dehydration of C4 Alkanois Conjucated With a Positional and Skeletal Isomerisation of the Formed C4 Alkenes"; Applied Catalysis A: General, Elsevier Science, Amsterdam, NL LNKD- DOI:10.1016/S0926-860X(01)00497-5; vol. 214, No. 2, pp. 251-257; Jun. 29, 2001; XP004241020; ISSN: 0926-860X.

Kai A.N. Verkerk, et al.; "Recent Developments in Isobutanol Synthesis From Synthesis Gas": Applied Catalysis A: General, Elsevier Science, vol. 186, pp. 407-431; 1999.

Sander Van Donk, et al; "Deactivation of Solid Acid Catalysts for Butene Skeletal Isomerisation: On the Beneficial and Harmful Effects of Carbonaceous Deposits"; Applied Catalysis A: General, Elsevier Science, vol. 212, pp. 97-116; 2001.

J. Warkentin, et al.; "Isobutane From Acid-Catalyzed Dehydration of Butanols"; Canadian Journal of Chemistry, vol. 48, pp. 3545-3548; XP002595037.

V.M. Gyznevskii, et al.; "Oxidation of Isobutyl Alcohol on Fe-Te-Mo-O Catalyst"; Database CA [Online]; Chemical Abstracts Service, Columbus, Ohio, US; 2003; retrieved from STN Database Accession No. 142:177154, abstract; & Kataliz I Neftekhimiya; vol. 12, pp. 74-77; Coden: KATNFD; XP002595038.

Edwin S. Olson, et al.; "Higher-Alcohols Biorefinery"; Applied Biochemistry and Biotechnology, vol. 113-116, pp. 913-932; 2004.

Shota Atsumi, et al.; "Non-Fermentative Pathways for Synthesis of Branched-Chain Higher Alcohols as Biofuels"; Nature, Letters, vol. 451, pp. 86-90; 2008.

Paul Meriaudeau, et al.; "Skeletal Isomerization of n-Butenes Catalyzed by Medium-Pore Zeolites and Aluminophosphates"; Advances in Catalysis, vol. 44; 2000; pp. 505-543.

J.H. De Boer, et al.; "Kinetics of the Dehydration of Alcohol on Alumina"; Journal of Catalysis, vol. 7; 1967; pp. 163-172.

Herman Pines, et al.; "Alumina: Catalyst and Support. IX. The Alumina Catalyzed Dehydration of Alcohols"; Journal of American Chemistry Soc., vol. 83; 1961, pp. 2847-2852.

Peter A. Jacobs; "Carboniogenic Activity of Zeolites"; Elsevier Scientific Publishing Company, Amsterdam-Oxford-New York; p. 169; 1977.

"Catalytic Activity and Selectivity"; Stud. Surf. Sci, Catal., vol. 51, p. 260; 1989.

Von Helmut Bahrmann, et al.; "Fortschritte der Homologisierungsreaktion"; Chemiker-Zeitung, vol. 106, No. 6; Jahrgang; 1982; pp. 249-258.

Carlo Carlini, et al.; "Selective Synthesis of Isobutanol by Means of the Guerbet Reaction Part 2. Reaction of Methanol/Ethanol and Methanol/Ethanol/n-Propanol Mixtures Over Copper Based/ MeONa Catalytic Systems"; Journal of Molecular Catalysis A: Chemical 200; pp. 137-146; 2003.

M. Guisnet, et al.; "Selective Skeletal Butene Isomerization Through a Bimolecular Mechanism"; Oil & Gas Science and Technology, vol. 54, No. 1; 1999; pp. 23-28.

Robert L. Banks, et al., "New Developments and Concepts in Enhancing Activities of Heterogeneous Metathesis Catalysts", Journal of Molecular Catalysis, vol. 28, pp. 117-131 (1985).

Ullmann's Encyclopedia of Industrial Chemistry, 6th edition, 2002.

Office Action issued in European Application No. 11708460.8, dated May 18, 2015, 4 pages.

Office Action issued in Chinese Patent Application No. 201180024167.6, dated Jan. 6, 2014 (19 pages).

Japanese Office Action issued in Japanese Application No. 204-234243, dated Aug. 21, 2015, 2 pages.

* cited by examiner

PRODUCTION OF PROPYLENE VIA SIMULTANEOUS DEHYDRATION AND SKELETAL ISOMERISATION OF ISOBUTANOL ON ACID CATALYSTS FOLLOWED BY METATHESIS

CROSS-REFERENCE TO RELATED APPLICATIONS

This application claims the benefit of PCT/EP2011/053905, filed Mar. 15, 2011, which claims priority from EP 10156537.2, filed Mar. 15, 2010, EP10159463.8, filed Apr. 9, 2010, EP 10159461.2, filed Apr. 9, 2010, EP 10160840.4, Filed Apr. 23, 2010, and EP 10161125.9, filed Apr. 27, 2010.

FIELD OF THE INVENTION

The present invention relates to the production of propylene via simultaneous dehydration and skeletal isomerisation of isobutanol to make a corresponding olefin, having substantially the same number of carbons but different skeleton structure, followed by a metathesis step. The limited supply and increasing cost of crude oil has prompted the search for alternative processes for producing hydrocarbon products such as propylene. Isobutanol can be obtained by fermentation of carbohydrates or by condensation of lighter alcohols, obtained by fermentation of carbohydrates. Made up of organic matter from living organisms, biomass is the world's leading renewable energy source.

BACKGROUND OF THE INVENTION

Isobutanol (2-methyl-1-propanol) has historically found limited applications and its use resembles that of 1-butanol. It has been used as solvent, diluent, wetting agent, cleaner additive and as additive for inks and polymers. Recently, isobutanol has gained interest as fuel or fuel component as it exhibits a high octane number (Blend Octane R+M/2 is 102-103) and a low vapor pressure (RVP is 3.8-5.2 psi).

Isobutanol is often considered as a byproduct of the industrial production of 1-butanol (Ullmann's encyclopedia of industrial chemistry, $6^{th}$ edition, 2002). It is produced from propylene via hydroformylation in the oxo-process (Rh-based catalyst) or via carbonylation in the Reppe-process (Co-based catalyst). Hydroformylation or carbonylation makes n-butanal and iso-butanal in ratios going from 92/8 to 75/25. To obtain isobutanol, the iso-butanal is hydrogenated over a metal catalyst. Isobutanol can also be produced from synthesis gas (mixture of CO, $H_2$ and $CO_2$) by a process similar to Fischer-Tropsch, resulting in a mixture of higher alcohols, although often a preferential formation of isobutanol occurs (Applied Catalysis A, general, 186, p. 407, 1999 and Chemiker Zeitung, 106, p. 249, 1982). Still another route to obtain isobutanol, is the base-catalysed Guerbet condensation of methanol with ethanol and/or propanol (J. of Molecular Catalysis A: Chemical 200, 137, 2003 and Applied Biochemistry and Biotechnology, 113-116, p. 913, 2004).

Recently, new biochemical routes have been developed to produce selectively isobutanol from carbohydrates. The new strategy uses the highly active amino acid biosynthetic pathway of microorganisms and diverts its 2-keto acid intermediates for alcohol synthesis. 2-Keto acids are intermediates in amino acid biosynthesis pathways. These metabolites can be converted to aldehydes by 2-keto-acid decarboxylases (KDCs) and then to alcohols by alcohol dehydrogenases (ADHs). Two non-native steps are required to produce alcohols by shunting intermediates from amino acid biosynthesis pathways to alcohol production (Nature, 451, p. 86, 2008 and US patent 2008/0261230). Recombinant microorganisms are required to enhance the flux of carbon towards the synthesis of 2-keto-acids. In the valine biosynthesis 2-ketoisovalerate is on intermediate. Glycolyse of carbohydrates results in pyruvate that is converted into acetolactate by acetolactate synthase. 2,4-dihydroxyisovalerate is formed out of acetolactate, catalysed by isomeroreductase. A dehydratase converts the 2,4-dihydroxyisovalerate into 2-keto-isovalerate. In the next step, a keto acid decarboxylase makes isobutyraldehyde from 2-keto-isovalerate. The last step is the hydrogenation of isobutyraldehyde by a dehydrogenase into isobutanol.

Of the described routes towards isobutanol above, the Guerbet condensation, the synthesis gas hydrogenation and the 2-keto acid pathway from carbohydrates are routes that can use biomass as primary feedstock. Gasification of biomass results in synthesis gas that can be converted into methanol or directly into isobutanol. Ethanol is already at very large scale produced by fermentation of carbohydrates or via direct fermentation of synthesis gas into ethanol. So methanol and ethanol resourced from biomass can be further condensed to isobutanol. The direct 2-keto acid pathway can produce isobutanol from carbohydrates that are isolated from biomass. Simple carbohydrates can be obtained from plants like sugar cane, sugar beet. More complex carbohydrates can be obtained from plants like maize, wheat and other grain bearing plants. Even more complex carbohydrates can be isolated from substantially any biomass, through unlocking of cellulose and hemicellulose from lignocelluloses.

In the mid nineties, many petroleum companies attempted to produce more isobutene for the production of MTBE. Hence many skeletal isomerisation catalysts for the conversion of n-butenes into iso-butene have been developed (Adv. Catal. 44, p. 505, 1999; Oil & Gas Science and Technology, 54 (1) p. 23, 1999 and Applied Catalysis A: General 212, 97, 2001). Among promising catalysts are 10-membered ring zeolites and modified alumina's. The reverse skeletal isomerisation of iso-butene into n-butenes has not been mentioned.

The dehydration reactions of alcohols to produce alkenes have been known for a long time (J. Catal. 7, p. 163, 1967 and J. Am. Chem. Soc. 83, p. 2847, 1961). Many available solid acid catalysts can be used for alcohol dehydration (Stud. Surf. Sci. Catal. 51, p. 260, 1989). However, γ-aluminas are the most commonly used, especially for the longer chain alcohols (with more than three carbon atoms). This is because catalysts with stronger acidity, such as the silica-aluminas, molecular sieves, zeolites or resin catalysts can promote double-bond shift, skeletal isomerization and other olefin inter-conversion reactions. The primary product of the acid-catalysed dehydration of isobutanol is iso-butene:

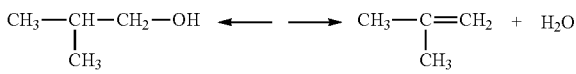

The dehydration of alcohols with four or more carbons over solid acid catalysts is expected to be accompanied by the double-bond shift reaction of the alkene product. This is because the two reactions occur readily and at comparable rates (Carboniogenic Activity of Zeolites, Elsevier Scientific Publishing Company, Amsterdam (1977) p. 169). The primary product, iso-butene is very reactive in presence of acid catalyst because of the presence of a double bond linked to a tertiary carbon. This allows easy protonation, as the tertiary structure of the resulting carbocation is the most favourable one among the possible carbocation structures (tertiary>secondary>primary carbocations). The resulting t-butyl-cation undergoes easy oligo/polymerisation or other electrophilic substitution on aromatics or aliphatics or electrophilic addition reactions. The rearrangement of t-butyl-cation is not a straightforward reaction as, without willing to be bound to any theory, involves an intermediate formation of secondary or primary butyl-cation and hence the probability of secondary reactions (substitutions or additions) is very high and would reduce the selectivity for the desired product.

Dehydration of butanols has been described on alumina-type catalysts (Applied Catalysis A, General, 214, p. 251, 2001). Both double-bond shift and skeletal isomerisation has been obtained at very low space velocity (or very long reaction time) corresponding to a GHSV (Gas Hourly Space Velocity=ratio of feed rate (gram/h) to weight of catalyst (ml)) of less than 1 gram·ml$^{-1}$·h$^{-1}$.

The U.S. Pat. No. 3,365,513 discloses that tungsten on silica is a suitable metathesis catalyst.

The FR2608595 patent discloses a process for making propylene by metathesis of 2-butene with ethylene over a catalyst containing Rhenium supported on a alumina containing carrier in a moving bed reaction zone at from 0 to 100° C., followed by a reoxidation of the catalyst at a higher temperature and reusing the catalyst.

EP304515 discloses a metathesis process for reacting 1-butene with 2-butene to give propene and pentenes, which is carried out in a reactive distillation apparatus using Re$_2$O$_7$/Al$_2$O$_3$ as catalyst.

U.S. Pat. No. 3,526,676 discloses the metathesis over MoO$_3$ and CoO on Al$_2$O$_3$ of 1-butene with 2-butene to give propene and pentene.

The U.S. Pat. No. 7,473,812 discloses a process to remove iso-butene from a butenes mixture by a process for coproducing butene oligomers and tert-butyl ethers by partly oligomerizing the iso-butene over an acidic catalyst to give butene oligomers and subsequently etherifying the remaining isobutene with an alcohol under acidic catalysis to give tert-butyl ethers.

The U.S. Pat. No. 6,159,433 discloses a process for the conversion of C4 or C5 cuts to an alkyl-t-butylether or alkyl-t-amylether and propylene by metathesis. The plant comprises four successive stages: (i) selective hydrogenation of diolefins with simultaneous isomerisation of the alpha olefins into internal olefins, (ii) etherification of the iso-olefins, (3) elimination of oxygen-containing impurities and (4) metathesis of internal olefins with ethylene.

The U.S. Pat. No. 6,495,732 describes a process to isomerise mono-olefins in aliphatic hydrocarbon streams at 40 to 300° F. under low hydrogen partial pressure in the range of about 0.1 psi to less than 70 psi at 0 to 350 psig in a distillation column reactor containing a hydrogenation catalyst which serves as a component of a distillation structure, such as supported PdO encased in tubular wire mesh. Essentially no hydrogenation of the mono-olefins occurs.

U.S. Pat. No. 4,469,911 discloses a process for isobutene oligomerization in the presence of a fixed bed cation exchange resin at a temperature in the range from 30° to 60° C. and a LHSV of from 2.5 to 12 h$^{-1}$.

U.S. Pat. No. 5,895,830 describes an enhanced dimer selectivity of a butene oligomerization process using SPA (supported phosphoric acid) catalyst, by diluting the butene feed with a heavy saturate stream comprising paraffins having a carbon number of at least 8.

U.S. Pat. No. 5,877,372 discloses dimerization of isobutene in the presence of isooctane diluent and tert-butyl alcohol (at least 1 wt-% and preferably 5 to 15 wt-%), over a sulfonic acid type ion exchange resin such as Amberlyst A-15, Dowex 50 or the like, at temperatures in the range 10° to 200° C. and pressures in the range of 50 to 500 psig. It is suggested that tert-butyl alcohol improves the selectivity of dimer formation and reduces the formation of trimer and higher oligomers.

U.S. Pat. No. 6,689,927 describes a low temperature butene oligomerization process having improved selectivity for dimerization and improved selectivity for the preferred 2,4,4-trimethylpentene isomer, caused by carrying out oligomerization in the presence of an SPA catalyst at a temperature below 112° C. in the presence of a saturated hydrocarbon diluent having a carbon number of at least 6.

The U.S. Pat. No. 7,220,886 discloses a process for the production of propylene from the metathesis of ethylene and 2-butene wherein a mixed C4 stream is first treated to enrich and separate the 2-butene from 1-butene and iso-butene and concurrent fractional distillation of the 2-butene and iso-butene to provide the 2-butene feed the metathesis with ethylene. In addition the mixed C4 stream may be treated to remove mercaptans and dienes prior to 2-butene enrichment.

U.S. Pat. No. 6,686,510 discloses a process for pretreating a metathesis feed and forming a high purity isobutene product. The olefinic C$_4$ stream is selectively hydrogenated to remove dienes and butynes and then distilled in a reaction distillation column that incorporates a catalyst for hydroisomerization of butene-1 to butene 2.

The international patent application WO 2005-110951 describes a process for the production of propylene via metathesis of n-butenes that have been obtained via skeletal isomerisation of iso-butene which is produced from t-butanol via dehydration.

Metathesis (co-metathesis) reaction between ethylene and butene-2 allows producing propylene from n-butenes. However, the presence of iso-butene has to be minimised in a metathesis reaction as iso-butene results in heavier hydrocarbons and hence loss of potential butene-2 that can make more propylene. The following show various metathesis reactions:

Co-Metathesis

Autometathesis

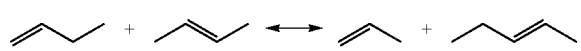

Heavies Formation During Metathesis in Presence of Iso-Butene

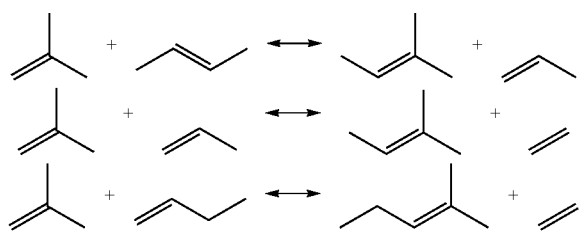

Tungsten based catalyst are one of the most preferred catalyst used in the industry. In particular, U.S. Pat. No. 4,575,575 and Journal of Molecular Catalysis, Vol. 28, p. 117 (1985)

describe the metathesis reaction between ethylene and 2-butene at 330° C. over silica-supported tungsten oxide catalyst, the conversion of butene being only 31%, while when magnesium oxide is used as a co-catalyst, the conversion increases to 67%. Moreover, U.S. Pat. No. 4,754,098 reports that for metathesis reaction at 330° C., the use of magnesium oxide, supported on γ-alumina increases the conversion of butene to 75%. It is also reported in U.S. Pat. No. 4,684,760 that lower temperature of 270° C. (the butene conversion is maintained at 74%) can be used when both magnesium oxide and lithium hydroxide are supported on γ-alumina.

Several techniques have been proposed to remove iso-butene upstream of a metathesis reactor. A first one is to convert the iso-butene into methyl-t-butyl-ether or ethyl-t-butyl-ether by reaction with methanol or ethanol respectively over acid-type catalysts. The ethers can be used as gasoline components. A second one is to convert iso-butene into oligomers over acid-type catalysts. The oligomers, mainly iso-octenes and iso-dodecenes can be used as gasoline component, either as such or after hydrogenation. A third one is the catalytic hydration of iso-butene into tertiary butylalcohol over acid-type catalyst. A fourth one is to distil the C4 fraction in a superfractionator. As the boiling points of iso-butene and 1-butene are very close, this can be done in a catalytic distillation column that converts the 1-butene continuously into 2-butene over a catalyst, the latter being significantly heavier than the iso-butene and goes to the bottom of the distillation tower. In a preferred method the isobutene is removed by catalytic distillation combining hydroisomerization and superfractionation. The hydroisomerization converts 1-butene to 2-butene, and the superfractionation removes the isobutene, leaving a relatively pure 2-butene stream. The advantage to converting the 1-butene to 2-butene in this system is that the boiling point of 2-butene (1° C. for the trans isomer, 4° C. for the cis isomer) is further away from the boiling point of isobutylene (−7° C.) than that of 1-butene (−6° C.), thereby rendering the removal of isobutene by superfractionation easier and less costly and avoiding the loss of 1-butene overhead with the isobutylene. The isomerisation catalyst, placed in the distillation column can be any catalyst that has isomerisation activity under the typical conditions of the distillation column. Preferred catalysts are palladium containing catalysts that are known to isomerise mono-olefins in the presence of small amounts of hydrogen. Often at the same time traces of diolefins can be converted into mono-olefins in presence of hydrogen.

It has now been discovered that the dehydration of isobutanol and the skeletal isomerisation of the iso-butyl moiety of isobutanol can be carried out simultaneously and that the resulting mixture of iso-butene and n-butenes, optionally depleted from iso-butene so that the remaining n-butenes can be efficiently used in the metathesis with ethylene or in autometathesis to produce propylene.

It is also part of the present invention that in the case an iso-butene enriched fraction is produced by distillation that this iso-butene fraction can be further converted into n-butenes by recycling it over the simultaneous dehydration/isomerisation reactor.

By way of example it has been discovered that for the simultaneous dehydration and skeletal isomerisation of isobutanol, crystalline silicates of the group FER, MWW, EUO, MFS, ZSM-48, MTT, MFI, MEL or TON having Si/Al higher than 10, or a dealuminated crystalline silicate of the group FER, MWW, EUO, MFS, ZSM-48, MIT, MFI, MEL or TON having Si/Al higher than 10, or a phosphorus modified crystalline silicate of the group FER, MWW, EUO, MFS, ZSM-48, MIT, MFI, MEL or TON having Si/Al higher than 10, or molecular sieves of the type silicoaluminophosphate of the group AEL or silicated, zirconated, titanated or fluorinated alumina's, have many advantages.

Said dehydration can be made with a WHSV (Weight Hourly Space Velocity=ratio of feed flow rate (gram/h) to catalyst weight) of at least 1 $h^{-1}$, at a temperature from 200 to 600° C. and using a isobutanol-diluent composition from 30 to 100% isobutanol at a total operating pressure from 0.05 to 1.0 MPa.

By way of example, in the dehydration/isomerisation of isobutanol on a ferrierite having a Si/Al ratio from 10 to 90 and with a WHSV of at least 2 $h^{-1}$ to make n-butenes beside iso-butene, the isobutanol conversion is at least 98% and often 99%, advantageously the butenes (iso and n-butenes) yield is at least 90%, the n-butenes selectivity is between 5% and the thermodynamic equilibrium at the given reaction conditions.

The isobutanol conversion is the ratio (isobutanol introduced in the reactor−isobutanol leaving the reactor)/(isobutanol introduced in the reactor).

The n-butenes yield is the ratio, on carbon basis, (n-butenes leaving the reactor)/(isobutanol introduced in the reactor).

The n-butenes selectivity is the ratio, on carbon basis, (n-butenes leaving the reactor)/(isobutanol converted in the reactor).

The simultaneous dehydration/isomerisation of isobutanol results in a mixture of n-butenes (but-1-ene and but-2-ene) and iso-butene. According to the present invention, often a composition close to thermodynamic equilibrium is obtained while maintaining the high yield of total butenes. The thermodynamic equilibrium for n-butenes varies between 50 and 65% and for iso-butene between 35 and 50% depending on operating conditions. An important advantage of the present invention is that the composition resembles the composition of a raffinate I C4 cut obtained from a steam naphtha cracker. Raffinate I is obtained by removing butadiene from the raw C4 cut produced on a steam naphtha cracker. Typical compositions are: 35-45% isobutane, 3-15% butanes and the remaining 52-40% n-butenes. Said product from the simultaneous dehydration/isomerisation can readily replace the use of raffinate I in existing petrochemical plants. The result is that capital investment can be minimised and that the derivatives from such iso-butene/n-butenes mixture can hence be produced from renewable resources instead of fossil resources simply by substituting fossil raffinate I by the product of the present invention.

EP 2090561 A1 describes the dehydration of an alcohol on crystalline silicates to get the corresponding olefin. Ethanol, propanol, butanol and phenylethanol are cited. Only ethanol is used in the examples. Nothing is cited about isobutanol and isomerisation thereof.

BRIEF SUMMARY OF THE INVENTION

The present invention relates to a process for the production of propylene in which in a first step isobutanol is subjected to a simultaneous dehydration and skeletal isomerisation to make substantially corresponding olefins, having the same number of carbons and consisting essentially of a mixture of n-butenes and iso-butene and in a second step n-butenes are subjected to methathesis, said process comprising:

a) introducing in a reactor a stream (A) comprising isobutanol, optionally water, optionally an inert component, b) contacting said stream with a catalyst in said reactor at conditions effective to dehydrate and skeletal isomerise at least a portion of the isobutanol to make a mixture of n-butenes and iso-butene, c) recovering from said reactor a stream (B), removing water, the inert component if any and unconverted isobutanol if any to get a mixture of n-butenes and iso-butene, d) fractionating said mixture to produce a n-butenes stream (N) and to remove the essential part of isobutene optionally recycled with stream (A) to the dehydration/isomerization reactor of step b), e) sending the stream (N) to a methathesis reactor and contacting stream (N) with a catalyst in said methathesis reactor, optionally in the presence of ethylene, at conditions effective to produce propylene, f) recovering from said methathesis reactor a stream (P) comprising essentially propylene, unreacted n-butenes, heavies, optionally unreacted ethylene, g) fractionating stream (P) to recover propylene and optionally recycling unreacted n-butenes and unreacted ethylene to the methathesis reactor.

In a first embodiment the WHSV of the isobutanol is at least 1 $h^{-1}$ and the catalyst in the dehydration/isomerization reactor is capable to make simultaneously the dehydration and skeletal isomerization of butene.

In a second embodiment, whichever is the isobutanol WHSV, the temperature ranges from 200° C. to 600° C. and the catalyst in the dehydration/isomerization reactor is capable to make simultaneously the dehydration and skeletal isomerization of butene.

Advantageously the dehydration/isomerization catalyst is a crystalline silicate of the group FER, MWW, EUO, MFS, ZSM-48, MTT, MFI, MEL or TON having Si/Al higher than 10, or a dealuminated crystalline silicate of the group FER, MWW, EUO, MFS, ZSM-48, MTT, MFI, MEL or TON having Si/Al higher than 10, or a phosphorus modified crystalline silicate of the group FER, MWW, EUO, MFS, ZSM-48, MTT, MFI, MEL or TON having Si/Al higher than 10, or a silicoaluminaphosphate molecular sieve of the group AEL, or a silicated, zirconated or titanated or fluorinated alumina.

It would not depart from the scope of the invention if the isobutanol feedstock comprises one or more of the other C4 alcohols such as 2-butanol, tertiary-butanol and n-butanol. Advantageously isobutanol is the major component among alcohols in the feedstock, this means the ratio of isobutanol to all the C4 alcohols in the feedstock is about 42% or above. More advantageously the previous ratio is 70% or more and preferably 80% or more. Of course if the proportion of isobutanol is too low the invention is of low interest, as the dehydration should then better be done without occurrence of skeletal isomerisation and there are a lot of catalysts in the prior art capable to dehydrate isobutanol, 2-butanol and n-butanol to produce the corresponding butenes. Dehydration of tertiary-butanol to isobutene followed by a skeletal isomerisation of at least a part of the tertiary-butanol is described in WO 2005110951.

In a specific embodiment, the mixture of n-butenes and iso-butene is fractionated into an iso-butene rich stream and a n-butenes rich stream or the iso-butene is selectively transformed in an easy separable product (iso-octenes, iso-dodecenes, t-butanol, MTBE or ETBE). The iso-butene rich stream can be recycled back over the simultaneous dehydration/isomerisation reactor to produce more n-butenes.

The n-butenes are sent to a metathesis reactor where they are converted into propylene by autometathesis or they are sent to a metathesis reactor where they are converted in the presence of added ethylene into propylene.

In a specific embodiment the n-butenes stream (N) of step d) comprises less than 10 w % of iso-butene and preferably less than 5 w %.

In a specific embodiment in the fractionation of step d) iso-butene is removed by selective oligomerisation of iso-butene. Said oligomerisation produces advantageously mainly iso-octenes and iso-dodecenes.

In a specific embodiment in the fractionation of step d) iso-butene is removed by selective etherification with methanol or ethanol.

In a specific embodiment in the fractionation of step d) iso-butene is removed by selective hydratation into t-butanol. Optionally said t-butanol is recycled to the dehydration/isomerization reactor of step b).

In a specific embodiment the metathesis is carried out as autometathesis with only butenes as feedstock.

In a specific embodiment the n-butenes stream (N) recovered at step d) is sent to an isomerisation unit to produce a n-butenes stream having a reduced 1-butene content and an enhanced 2-butene content, then said stream is sent to the methathesis reactor.

In a specific embodiment the fractionation of step d) is made by a catalytic distillation column wherein the essential part of 1-butene is isomerised to 2-butene, iso-butene is recovered as overhead and 2-butene is recovered in the bottoms of said column. Advantageously iso-butene is recycled to the dehydration/isomerization reactor of step b).

In a specific embodiment the metathesis is carried out by adding ethylene to the butenes. Advantageously the butenes are essentially 2-butene.

DETAILED DESCRIPTION OF THE INVENTION

Figure 1:
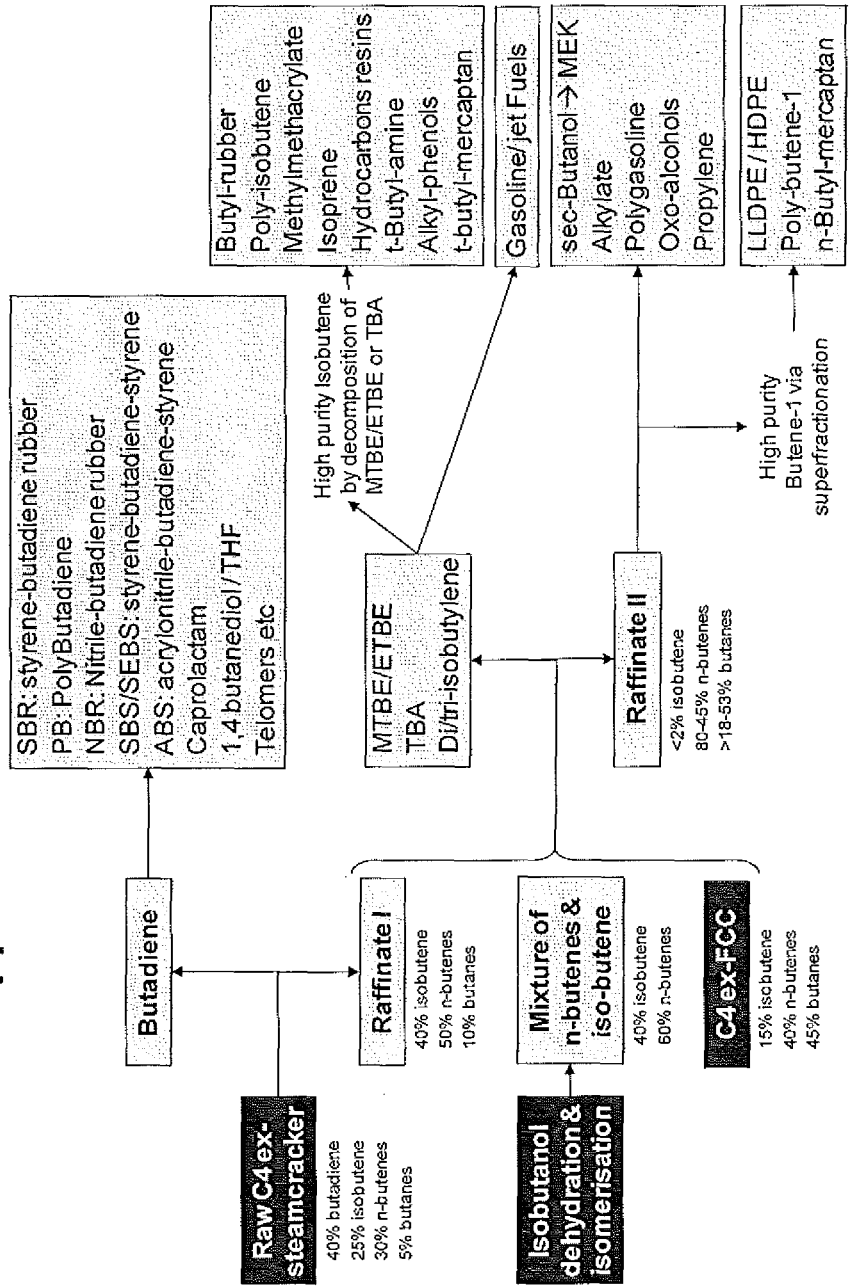
FIG. 1 depicts applications of n-butenes and isobutene.

As regards the stream (A), the isobutanol may be subjected to simultaneous dehydration and skeletal isomerisation alone or in mixture with an inert medium. The inert component is any component provided it is substantially not converted on the catalyst. Because the dehydration step is endothermic the inert component can be used as energy vector. The inert component allows reducing the partial pressure of the isobutanol and other reaction intermediates and will hence reduce secondary reactions like oligo/polymerisation. The inert component may be selected among water, nitrogen, hydrogen, CO2 and saturated hydrocarbons. It may be such that some inert components are already present in the isobutanol because they were used or co-produced during the production of isobutanol. Examples of inert components that may already be present in the isobutanol are water and CO2. The inert component may be selected among the saturated hydrocarbons having up to 10 carbon atoms, naphtenes. Advantageously it is a saturated hydrocarbon or a mixture of saturated hydrocarbons having from 3 to 7 carbon atoms, more advantageously having from 4 to 6 carbon atoms and is preferably pentane. An example of inert component can be any individual saturated compound, a synthetic mixture of the individual saturated compounds as well as some equilibrated refinery streams like straight naphtha, butanes etc. Advantageously the inert component is a saturated hydrocarbon having from 3 to 6 carbon atoms and is preferably pentane. The weight proportions of respectively isobutanol and inert component are, for example, 30-100/70-0 (the total being 100). The stream (A) can be liquid or gaseous.

As regards the reactor for the simultaneous dehydration/isomerisation, it can be a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. The simultaneous dehydration/isomerisation may be performed continuously in a fixed bed reactor configuration using a pair of parallel "swing" reactors. The various preferred catalysts of the present invention have been found to exhibit high stability. This enables the dehydration process to be performed continuously in two parallel "swing" reactors wherein when one reactor is operating, the other reactor is undergoing catalyst regeneration. The catalyst of the present invention also can be regenerated several times.

The simultaneous dehydration/isomerisation may be performed continuously in a moving bed reactor in which the catalyst circulates from a reaction zone to a regeneration zone and backwards with a residence time of the catalyst in the reaction zone of at least 12 hours. In each zone the catalyst behaves substantially like in a fixed bed reactor, but the catalyst moves slowly, by gravity or pneumatically through the respective zone. The use of a moving bed reaction allows accomplishing a continuous operation with no switching of the feedstock and regeneration gas from one reactor to another one. The reaction zone receives continuously the feedstock while the regeneration zone receives continuously the regeneration gas.

The simultaneous dehydration/isomerisation may be performed continuously in a fluidised bed reactor in which the catalyst circulates from a reaction zone to a regeneration zone and backwards with a residence time of the catalyst in the reaction zone of less than 12 hours. In each zone the catalyst is in a fluidised state and exhibit such a shape and size that it remains fluidised in the flow of the feedstock and reaction products or regeneration gas. The use of a fluidised bed reactor allows regenerating very rapidly deactivated catalyst by regeneration in the regeneration zone.

As regards the pressure for the simultaneous dehydration/isomerisation, it can be any pressure but it is more easy and economical to operate at moderate pressure. By way of example the pressure of the reactor ranges from 0.5 to 10 bars absolute (50 kPa to 1 MPa), advantageously from 0.5 to 5 bars absolute (50 kPa to 0.5 MPa), more advantageously from 1.2 to 5 bars absolute (0.12 MPa to 0.5 MPa) and preferably from 1.2 to 4 bars absolute (0.12 MPa to 0.4 MPa). Advantageously the partial pressure of the isobutanol is from 0.1 to 4 bars absolute (0.01 MPa to 0.4 MPa), more advantageously from 0.5 to 3.5 bars absolute (0.05 MPa to 0.35 MPa).

As regards the temperature for the simultaneous dehydration/isomerisation, and the first embodiment it ranges from 200° C. to 600° C., advantageously from 250° C. to 500° C., more advantageously from 300° C. to 450° C. As regards the temperature and the second embodiment it ranges from 200° C. to 600° C., advantageously from 250° C. to 500° C., more advantageously from 300° C. to 450° C.

These reaction temperatures refer substantially to average catalyst bed temperature. The isobutanol dehydration is an endothermic reaction and requires the input of reaction heat in order to maintain catalyst activity sufficiently high and shift the dehydration thermodynamic equilibrium to sufficiently high conversion levels.

In case of fluidised bed reactors: (i) for stationary fluidised beds without catalyst circulation, the reaction temperature is substantially homogeneous throughout the catalyst bed; (ii) in case of circulating fluidised beds where catalyst circulates between a converting reaction section and a catalyst regeneration section, depending on the degree of catalyst backmixing the temperature in the catalyst bed approaches homogeneous conditions (a lot of backmixing) or approaches plug flow conditions (nearly no backmixing) and hence a decreasing temperature profile will install as the conversion proceeds.

In case of fixed bed or moving bed reactors, a decreasing temperature profile will install as the conversion of the isobutanol proceeds. In order to compensate for temperature drop and consequently decreasing catalyst activity or approach to thermodynamic equilibrium, reaction heat can be introduced by using several catalyst beds in series with interheating of the reactor effluent from the first bed to higher temperatures and introducing the heated effluent in a second catalyst bed, etc. When fixed bed reactors are used, a multi-tubular reactor can be used where the catalyst is loaded in small-diameter tubes that are installed in a reactor shell. At the shell side, a heating medium is introduced that provides the required reaction heat by heat-transfer through the wall of the reactor tubes to the catalyst.

As regards the WHSV of the isobutanol for the simultaneous dehydration/isomerisation, and the first embodiment it ranges advantageously from 1 to 30 $h^{-1}$, preferably from 2 to 21 $h^{-1}$, more preferably from 7 to 12 $h^{-1}$. As regards the second embodiment it ranges advantageously from 1 to 30 $h^{-1}$, more advantageously from 2 to 21 $h^{-1}$, preferably from 5 to 15 $h^{-1}$, more preferably from 7 to 12 $h^{-1}$.

As regards the stream (B) from the simultaneous dehydration/isomerisation, it comprises essentially water, olefin, the inert component (if any) and unconverted isobutanol. Said unconverted isobutanol is supposed to be as less as possible. The olefin is recovered by usual fractionation means. Advantageously the inert component, if any, is recycled in the stream (A) as well as the unconverted isobutanol, if any. Unconverted isobutanol, if any, is recycled to the reactor in the stream (A).

Advantageously among the butenes the proportion of n-butenes is above 20%, advantageously above 30%, more advantageously above 40%, preferably above 50%.

As regards the catalyst for the simultaneous dehydration/isomerisation, advantageously it is a crystalline silicate of the group FER (ferrierite, FU-9, ZSM-35), MWW (MCM-22, PSH-3, ITQ-1, MCM-49), EUO (ZSM-50, EU-1), MFS (ZSM-57), ZSM-48, MTT (ZSM-23), MFI (ZSM-5), MEL (ZSM-11) or TON (ZSM-22, Theta-1, NU-10), or a dealuminated crystalline silicate of the group FER (ferrierite, FU-9, ZSM-35), MWW (MCM-22, PSH-3, ITQ-1, MCM-49), EUO (ZSM-50, EU-1), MFS (ZSM-57), ZSM-48, MIT (ZSM-23), MFI (ZSM-5), MEL (ZSM-11) or TON (ZSM-22, Theta-1, NU-10), or a phosphorus modified crystalline silicate of the group FER (ferrierite, FU-9, ZSM-35), MWW (MCM-22, PSH-3, ITQ-1, MCM-49), EUO (ZSM-50, EU-1), MFS (ZSM-57), ZSM-48, MTT (ZSM-23), MFI (ZSM-5), MEL (ZSM-11) or TON (ZSM-22, Theta-1, NU-10), or a silicoaluminophosphate molecular sieve of the group AEL (SAPO-11),
or a silicated, zirconated or titanated or fluorinated alumina.

A preferred catalyst is a crystalline silicate of the group FER or MFI having Si/Al higher than 10,
or a dealuminated crystalline silicate of the group FER or MFI having Si/Al higher than 10,
or a phosphorus modified crystalline silicate of the group FER or MFI having Si/Al higher than 10, About the crystalline silicate of FER structure (ferrierite, FU-9, ZSM-35) it can be the lamellar precursor which becomes FER by calcinations.

The Si/Al ratio of the crystalline silicate is advantageously higher than 10.

The crystalline silicate is such as the Si/Al ratio ranges more advantageously from 10 to 500, preferably from 12 to 250, more preferably from 15 to 150.

The acidity of the catalyst can be determined by the amount of residual ammonia on the catalyst following contact of the catalyst with ammonia which adsorbs on the acid sites of the catalyst with subsequent ammonium desorption at elevated temperature measured by differential thermogravimetric analysis or analysis of ammonia concentration in the desorbed gases.

The crystalline silicate can be subjected to various treatments before use in the dehydration including, ion exchange, modification with metals (in a not restrictive manner alkali, alkali-earth, transition, or rare earth elements), external surface passivation, modification with P-compounds, steaming, acid treatment or other dealumination methods, or combination thereof.

In a specific embodiment the crystalline silicate is steamed to remove aluminium from the crystalline silicate framework. The steam treatment is conducted at elevated temperature, preferably in the range of from 425 to 870° C., more preferably in the range of from 540 to 815° C. and at atmospheric pressure and at a water partial pressure of from 13 to 200 kPa. Preferably, the steam treatment is conducted in an atmosphere comprising from 5 to 100 vol % steam. The steam atmosphere preferably contains from 5 to 100 vol % steam with from 0 to 95 vol % of an inert gas, preferably nitrogen. The steam treatment is preferably carried out for a period of from 1 to 200 hours, more preferably from 4 hours to 10 hours. As stated above, the steam treatment tends to reduce the amount of tetrahedral aluminium in the crystalline silicate framework, by forming alumina.

In a more specific embodiment the crystalline silicate is dealuminated by heating the catalyst in steam to remove aluminium from the crystalline silicate framework and extracting aluminium from the catalyst by contacting the catalyst with a complexing agent for aluminium to remove from pores of the framework alumina deposited therein during the steaming step thereby to increase the silicon/aluminium atomic ratio of the catalyst. In accordance with the present invention, the commercially available crystalline silicate is modified by a steaming process which reduces the tetrahedral aluminium in the crystalline silicate framework and converts the aluminium atoms into octahedral aluminium in the form of amorphous alumina. Although in the steaming step aluminium atoms are chemically removed from the crystalline silicate framework structure to form alumina particles, those particles cause partial obstruction of the pores or channels in the framework. This could inhibit the dehydration process of the present invention. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminium complex yields the overall effect of de-alumination of the crystalline silicate. In this way by removing aluminium from the crystalline silicate framework and then removing alumina formed therefrom from the pores, the process aims at achieving a substantially homogeneous de-alumination throughout the whole pore surfaces of the catalyst. This reduces the acidity of the catalyst. The reduction of acidity ideally occurs substantially homogeneously throughout the pores defined in the crystalline silicate framework. Following the steam treatment, the extraction process is performed in order to de-aluminate the catalyst by leaching. The aluminium is preferably extracted from the crystalline silicate by a complexing agent which tends to form a soluble complex with alumina. The complexing agent is preferably in an aqueous solution thereof. The complexing agent may comprise an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The complexing agent may comprise an inorganic acid such as nitric acid, halogenic acids, sulphuric acid, phosphoric acid or salts of such acids or a mixture of such acids. The complexing agent may also comprise a mixture of such organic and inorganic acids or their corresponding salts. The complexing agent for aluminium preferably forms a water-soluble complex with aluminium, and in particular removes alumina which is formed during the steam treatment step from the crystalline silicate.

Following the aluminium leaching step, the crystalline silicate may be subsequently washed, for example with distilled water, and then dried, preferably at an elevated temperature, for example around 110° C.

Additionally, if during the preparation of the catalysts of the invention alkaline or alkaline earth metals have been used, the molecular sieve might be subjected to an ion-exchange step. Conventionally, ion-exchange is done in aqueous solutions using ammonium salts or inorganic acids.

Following the de-alumination step, the catalyst is thereafter calcined, for example at a temperature of from 400 to 800° C. at atmospheric pressure for a period of from 1 to 10 hours.

Another suitable catalyst for the present process is the silicoaluminophosphate molecular sieves of the AEL group with typical example the SAPO-11 molecular sieve. The SAPO-11 molecular sieve is based on the ALPO-11, having essentially an Al/P ratio of 1 atom/atom. During the synthesis silicon precursor is added and insertion of silicon in the ALPO framework results in an acid site at the surface of the micropores of the 10-membered ring sieve. The silicon content ranges from 0.1 to 10 atom % (Al+P+Si is 100).

In another specific embodiment the crystalline silicate or silicoaluminophosphate molecular sieve is mixed with a binder, preferably an inorganic binder, and shaped to a desired shape, e.g. pellets. The binder is selected so as to be resistant to the temperature and other conditions employed in the dehydration process of the invention. The binder is an inorganic material selected from clays, silica, metal silicates, metal oxides such as $ZrO_2$ and/or metals, or gels including mixtures of silica and metal oxides. If the binder which is used in conjunction with the crystalline silicate is itself catalytically active, this may alter the conversion and/or the selectivity of the catalyst. Inactive materials for the binder may suitably serve as diluents to control the amount of conversion so that products can be obtained economically and orderly without employing other means for controlling the reaction rate. It is desirable to provide a catalyst having a good crush strength. This is because in commercial use, it is desirable to prevent the catalyst from breaking down into powder-like materials. Such clay or oxide binders have been employed normally only for the purpose of improving the crush strength of the catalyst. A particularly preferred binder for the catalyst of the present invention comprises silica. The relative proportions of the finely divided crystalline silicate material and the inorganic oxide matrix of the binder can vary widely. Typically, the binder content ranges from 5 to 95% by weight, more typically from 20 to 75% by weight, based on the weight of the composite catalyst. Such a mixture of the crystalline silicate and an inorganic oxide binder is referred to as a formulated crystalline silicate. In mixing the catalyst with a binder, the catalyst may be formulated into pellets, extruded into other shapes, or formed into spheres or a spray-dried powder. Typically, the binder and the crystalline silicate are mixed together by a mixing process. In such a process, the binder, for example silica, in the form of a gel is mixed with the crystalline silicate material and the resultant mixture is extruded into the desired shape, for example cylindrical or multi-lobe bars. Spherical shapes can be made in rotating granulators or by oil-drop technique. Small spheres can further be made by spray-drying a catalyst-binder suspension. Thereafter, the formulated crystalline silicate is calcined in air or an inert gas, typically at a temperature of from 200 to 900° C. for a period of from 1 to 48 hours.

In addition, the mixing of the catalyst with the binder may be carried out either before or after the steaming and extraction steps.

Another family of suitable catalysts for the simultaneous dehydration and skeletal isomerisation are alumina's that have been modified by surface treatment with silicon, zirconium, titanium or fluor. Alumina's are generally characterised by a rather broad acid strength distribution and having both Lewis-type and Bronsted-type acid sites. The presence of a broad acid strength distribution makes the catalysis of several reactions, requiring each a different acid strength, possible. This often results in low selectivity for the desired product. Deposition of silicon, zirconium, titanium or fluor on the surface of alumina allows rendering the catalyst significantly more selective. For the preparation of the alumina based catalyst, suitable commercial alumina's can be used, preferably eta or gamma alumina, having a surface area of 10 to 500 m2/gram and an alkali content of less than 0.5%. The catalyst according to the present invention is prepared by adding 0.05 to 10% of silicon, zirconium or titanium. The addition of these metals can be done during the preparation of the alumina or can be added to the existing alumina, eventually already activated. Addition of the metal during the preparation of the alumina can be done by dissolving the metal precursor together with the aluminium precursor before precipitation of the final alumina or by addition of the metal precursor to the aluminium hydroxide gel. A preferred method is adding metal precursors to the shaped alumina. Metal precursors are dissolved in a suitable solvent, either aqueous or organic, and contacted with the alumina by incipient wetness impregnation or by wet impregnation or by contacting with an excess of solute during a given time, followed by removing the excess solute. The alumina can also be contacted with vapour of the metal precursor. Suitable metal precursors are halides of silicon, zirconium or titanium, oxyhalides of zirconium or titanium; alcoxides of silicon, zirconium or titanium; oxalates or citrates of zirconium or titanium or mixtures of the above. The solvent is selected according to the solubility of the metal precursor. The contacting can be done at temperature of 0° C. to 500° C., most preferred from 10° C. to 200° C. After the contacting, the alumina is eventually washed, dried and finally calcined in other to enhance the surface reaction between the silicon, zirconium or titanium and the alumina and the removal of the metal precursor ligands. The use of silicated, zirconated or titanated or fluorinated alumina's for the simultaneous dehydration and skeletal isomerisation of isobutanol is preferably done in the presence of water. The weight ratio of water to isobutanol ranges from 1/25 to 3/1. Fluorinated alumina is known in itself and can be made according to the prior art.

As regards the use of the product from the simultaneous dehydration/isomerisation, the mixture of n-butenes and iso-butene can replace the use of raffinate I in the refinery or petrochemical plants. FIG. 1 shows the main applications of n-butenes and isobutene. The most typical application of such mixture is the conversion of the contained iso-butene into ethers (MTBE and ETBE), into t-butylalcohol (TBA) or oligomers (e.g. di/tri-iso-butenes), all being gasoline components. The higher oligomers of iso-butene can be used for jet fuel/kerosene applications. High purity iso-butene can further be made by the decomposition of ethers (backcracking) or TBA (dehydration). High purity iso-butene finds applications in the production of Butyl-rubber, Poly-isobutene, Methyl-methacrylate, Isoprene, Hydrocarbons resins, t-Butyl-amine, Alkyl-phenols and t-butyl-mercaptan.

The n-butenes, having not reacted during the production of ethers or TBA and substantially not or only to a limited extend during the oligomerisation, have applications in the production of sec-Butanol, Alkylate (addition of isobutane to butenes), Polygasoline, Oxo-alcohols and Propylene (metathesis with ethylene or self-metathesis between but-1-ene and but-2-ene). By means of superfractionation or extractive distillation or absorptive separation but-1-ene can be isolated from the n-butenes mixture. But-1-ene is used as comonomer for the production of polyethylenes, for poly-but-1-ene and n-butyl-mercaptan.

n-Butenes can also be separated from iso-butene by means of a catalytic distillation. This involves an isomerisation catalyst that is located in the distillation column and continuously converts the but-1-ene into but-2-ene, being a heavier component than but-1-ene. Doing so, a bottom product rich in but-2-ene and a top product poor in but-1-ene and rich in iso-butene is produced. The bottom product can be used as described above. One main application of such but-2-ene rich stream is the metathesis with ethylene in order to produce propylene. If high purity iso-butene is desired the top product can be further superfractionated into substantially pure iso-butene and pure but-1-ene or the iso-butene can be isolated via formation of ethers or TBA that is subsequently decomposed into pure iso-butene.

The n-butenes rich stream may be used for the production of butadiene via dehydrogenation or oxidative dehydrogenation.

The mixture of isobutene and butenes can be sent to a catalytic cracking which is selective towards light olefins in the effluent, the process comprising contacting said isobutene and butenes mixture with an appropriate catalyst to produce an effluent with an olefin content of lower molecular weight than that of the feedstock. Said cracking catalyst can be a silicalite (MFI or MEL type) or a P-ZSM5.

As regards the preparation of the metathesis feedstock, it is preferred to remove the iso-butene before metathesis. This can be done by a selective chemical transformation of iso-butene or by distillation. Selective chemical transformations are: (i) oligomerisation, (ii) etherification or (iii) hydration or combinations of them. The resulting products are respectively: (i) iso-octenes for use in gasoline, tri, tetra or pentamers of substantially iso-butene for use in Jet fuel or kerozine; (ii) methyl-t-butylether or ethyl-t-butylether; (iii) t-butanol. The oligomers are eventually hydrogenated to the corresponding paraffin's. The t-butanol can eventually be recycled back into the simultaneous dehydration/skeletal isomerisation reaction sections.

A preferred distillation method is the catalytic distillation during which the 1-butene is continuously transformed into 2-butenes so as to optimise the 2-butenes yield and minimise entrainment of 1-butene with the overhead iso-butene. The iso-butene rich overhead can be recycling back to the simultaneous dehydration/skeletal isomerisation reaction sections.

As regards the metathesis catalyst, three types of metal containing catalysts can be suitable to perform the disproportionation reaction. The co-metathesis reaction of the ethylene with the butene-2 or the autometathesis of a mixture of 1-butene and 2-butene can be catalyzed by three metallic oxides that are dispersed on carriers: by molybdenum (eventually in combination with cobalt and rhenium), tungsten or rhenium oxides.

A first kind of catalyst is Rhenium supported on alumina-containing carrier. The Rhenium content can be from 0.5 to 15 wt %. The Rhenium catalyst is before use heat treated at a temperature of at least 400° C., preferably at least at 500° C. Optionally the catalyst can be activated before use by treating it with alkyl-boron, alkyl-aluminium or alkyl-tin compounds. The rhenium oxide is deposited on a substrate that comprises a refractory oxide, containing at least alumina and exhibiting an acidic nature, such as, for example, alumina, silica-alumina's or zeolites.

By way of preferred examples, the catalysts comprise rhenium heptoxide that is deposited on a gamma-alumina, such as those described in U.S. Pat. No. 4,795,734. The rhenium content can be 0.01 to 20 wt %, preferably 1 to 15 wt %.

The catalysts that comprise rhenium heptoxide that is deposited on an alumina can also be modified by the addition of a metal oxide. 0.01 to 30 wt % of at least one metal oxide of the niobium or tantalum group can be added according to FR2709125. FR2740056 describes that 0.01 to 10% by weight of aluminium of a compound of formula $(RO)_q AlR'_r$, where R is a hydrocarbyl radical of 1 to 40 carbon atoms, R' is an alkyl radical of 1 to 20 carbon atoms, and q and r are equal to 1 or 2, with q+r equal to 3, can be added.

The metathesis reaction over rhenium heptoxide catalysts is carried out preferably in a liquid phase, in absence of oxygen-containing compounds and moisture, and at a temperature of 0 to 150° C., preferably 20 to 100° C., under a pressure at least to keep the reaction mixture at the reaction temperature in the liquid state.

A second type of catalyst is tungsten supported on silica carrier. The tungsten content can be from 1 to 15 wt %. The tungsten based catalyst is heat treated before use at least at 300° C., preferably at least at 500° C. The catalyst can further be activated by treatment with hydrogen, carbon monoxide or by ethylene.

The tungsten based catalysts are advantageously used in combination with a co-catalyst. Examples of co-catalysts used in the invention include compounds of metal belonging to Group Ia (alkali metals), Group IIa (alkaline earth metals), Group IIb and Group IIIa of the periodic table or combinations of the latter. Lithium, sodium, potassium, cesium, magnesium, calcium, strontium, barium, zinc, lanthanum and yttrium are preferred. These metals are generally used as oxides, as such or deposited on a carrier or as mixed oxides. Examples of the latter are hydrotalcites that are double layered hydroxide of aluminium and magnesium, and solid solutions of aluminium oxide and magnesium oxide obtained by calcining the corresponding hydrotalcite. The oxides, mixed oxides, hydroxides, double hydroxides, nitrates and acetates of the metals may be supported on carriers having a large surface area.

U.S. Pat. No. 4,575,575, U.S. Pat. No. 4,754,098 and U.S. Pat. No. 4,684,760 describe that magnesium oxide is essentially used as a co-catalyst. In any of U.S. Pat. No. 4,575,575, U.S. Pat. No. 4,575,575, U.S. Pat. No. 4,754,098, U.S. Pat. No. 4,754,098 and U.S. Pat. No. 4,684,760, magnesium oxide containing a promoter is mentioned as an essential component The carrier for the co-catalyst is preferably a compound that does not possess acidity, because acid sites may induce oligomerization of olefins. Preferred examples of the carriers for the co-catalysts include carbon, basic zeolites, γ-alumina, silica, alkaline earth or alkali silicates, alumino-phosphates, zirconia and titania. The amount of the co-catalyst metal oxide deposited on the carrier is generally in the range of 0.01 to 40 wt %, and is preferably in the range of 0.1 to 20 wt %.

The metal compound for making the co-catalyst can be supported on the carrier by various methods. Metal precursors can be any salt, as examples nitrates, halides, oxyhalides or hydroxides. Also alcoxy (RO) compounds can be used as precursor. The starting material is dissolved into a suitable solvent, preferably an aqueous solution, and the carrier is impregnated therewith. The excess of solvent, if any, is then evaporated to dryness, and the residue is calcined at a temperature of 300° C. or higher in an oxygen atmosphere.

When the carrier is prepared from a metal salt or alcoxy precursors, a coprecipitation method can be used. Hereto, metal salts or alcoxy compounds of both the carrier and the catalytic active metal are mixed and caused to precipitate simultaneously.

The shapes of the co-catalyst can be essentially any shape such as spherical shapes, cylindrical shapes, extruded shapes and pellets. It is preferable that the shape of the particles is such that the co-catalyst can be easily mixed with the metathesis catalyst or can be installed above or below the catalyst bed containing the metathesis catalyst.

In the metathesis process, the weight ratio of the co-catalyst to the metathesis catalyst is advantageously from 0.1 to 15, preferably from 1 to 8.

Without willing to be bound to any theory, it is believed that the co-catalyst as of its basic nature exhibits two activities: (i) the isomerisation of alpha-olefins into internal olefins, the latter will result in the disproportionation reaction with ethylene, the desired shorter alpha-olefin, namely propylene, (ii) capturing poisons for the metathesis like any compound that has some acidic nature as $CO_2$, $H_2S$, $H_2O$ etc.

When the metathesis catalyst and co-catalyst are packed into a fixed bed flow reactor, a physically mixture of the metathesis catalyst and the co-catalyst may be loaded, as described in the Journal of Molecular Catalysis, Volume 28, page 117 (1985), or a layer of the co-catalyst may be packed on top of the metathesis catalyst. In addition, a combination of these methods may be used.

A third type of catalyst is molybdenum supported on alumina or silica carrier. Suitable molybdenum oxide based catalysts are disclosed in U.S. Pat. No. 3,658,927 and U.S. Pat. No. 4,568,788. The disproportionation catalyst in the instant invention is prepared by using at least one of molybdenum, eventually combined with cobalt or rhenium, supported on an inorganic oxide support. The inorganic oxide support comprises a substantial amount of silica or alumina. Synthetic refractory oxides include silica, alumina, silica-alumina, silica-magnesia, silica-titania, alumina-titania, alumina-magnesia, boria-alumina-silica, alumina-zirconia, thoria and silica-titania-zirconia. The molybdenum, eventually in combination with cobalt or rhenium can be dispersed on the inorganic oxide support by any conventional method such as impregnation, dry mixing, ion-exchange, coprecipitation. For example, alumina can be impregnated with an aqueous solution containing molybdenum salts, such as ammonium heptamolybdate or ammonium dimolybdate. Once the molybdenum is dispersed on the carrier it is calcined at least at 300° C. and before use in the metathesis reaction, it may be activated by contacting with alkyl-boron, alkyl-aluminium or alkyl-tin compounds. The metal compound for the making of molybdenum, rhenium or tungsten based metathesis catalyst can be supported on the carrier by various methods. Metal precursors can be any salt, as examples nitrates, halides, oxyhalides or hydroxides. Also polyacids or isopolyacids or the corresponding ammonium salt of the polyacid, or ammonium salt of the isopolyacid can be used as a starting material. Also alcoxy (RO) compounds can be used as precursor. The starting material is dissolved into a suitable solvent, preferably an aqueous solution, and the carrier is impregnated therewith. The excess of solvent, if any, is then evaporated to dryness, and the residue is calcined at a temperature of 300° C. or higher in an oxygen atmosphere.

When the carrier is prepared from a metal salt or alcoxy precursors, a coprecipitation method can be used. Hereto, metal salts or alcoxy compounds of both the carrier and the catalytic active metal are mixed and caused to precipitate simultaneously.

The carrier is generally formed into essentially any shape such as spherical shapes, cylindrical shapes, extruded shapes and pellets. The size of the shaped particles is related to the reactor type and is generally in the range of 0.01 to 10 mm.

The activity of the metathesis catalyst is generally decreased by polar compounds like moisture, carbon dioxide, carbon monoxide, diene compounds, sulphur and nitrogen compounds, alcohols, aldehydes and carboxylic compounds. Accordingly, the olefins used as feedstock preferably should be purified from impurities. Such impurities are removed by distillation, adsorption, extraction or washing. Other materials used during the process like nitrogen gas and hydrogen gas that are introduced into the reactor need also extensive purification. Nitrogen is often needed to purge reactors from moisture, reducing agents (carbon monoxide, ethylene or hydrogen) and resulting residues from this reduction.

The most suitable adsorbent to be used is γ-alumina or promoted alumina's, which is particularly suitable for the removal of polar substances such as water, mercaptans, aldehydes and alcohols. Also, magnesium oxide based adsorbents, are suitable for removal of not only neutral polar substances such as water and the like but also acidic substances such as carbon dioxide, organic acids and the like. Also, zeolite compounds, for example, Molecular Sieve 4A, 5A, 13X and the like are not only excellent in adsorption of neutral polar substances such as water and the like but also very effective in adsorbing basic compounds because their acidic property. Suitable not restricting examples of zeolite used are from the A type, X type, Y type, USY type, ZSM-5 type and the like.

Furthermore, the activity of the metathesis catalyst can further be increased or stabilised by in the presence of hydrogen. The amount of hydrogen in the combined feedstock of olefins (butenes and ethylene) is advantageously in the range of 0.1 to 10 vol % and preferably 0.2 to 5 vol %.

The metathesis reaction can be carried out in liquid phase, gas phase, and mixed gas-liquid phase, which is determined by the reaction temperature and pressure. Rhenium based catalyst performs preferably between 0 and 150° C. at a pressure to keep the feedstock in the liquid state. Molybdenum based catalyst perform preferably at 100 to 250° C. in the gas phase at from 1 to 30 bars pressure. Tungsten based catalysts perform preferably at 150 to 400° C. at a pressure of from 5 to 35 bars. The metathesis may be performed continuously in a fixed bed reactor configuration using a pair of parallel "swing" reactors, provided the catalyst exhibits sufficient stability of at least 2 days. This enables the methathesis process to be performed continuously in two parallel "swing" reactors wherein when one reactor is operating; the other reactor is undergoing catalyst regeneration. When the catalyst stability is shorter than about 2 days, metathesis may also be performed continuously in a moving bed reactor in which the catalyst circulates from a reaction zone to a regeneration zone and backwards with a residence time of the catalyst in the reaction zone of at least 5 hours. In each zone the catalyst behaves substantially like in a fixed bed reactor, but the catalyst moves slowly, by gravity or pneumatically through the respective zone. The use of a moving bed reaction allows accomplishing a continuous operation with no switching of the feedstock and regeneration gas from one reactor to another one. The reaction zone receives continuously the feedstock while the regeneration zone receives continuously the regeneration gas.

The metathesis can be done with only a mixture of n-butenes and is commonly known as autometathesis. The products are propylene and pentenes. The propylene desired product is recovered while the pentenes can be recycled back to the metathesis reaction section. The metathesis can also been carried out by adding ethylene to the n-butenes feedstock, commonly known as co-metathesis. The molar ratio of ethylene to n-butenes is advantageously from 0.75 to 5, preferably from 1 to 2.5.

As regards the products of the metathesis reaction, the reactor effluent contains non-converted ethylene, if any was added to the reaction section, and butenes, some heavies and the desired propylene product. In a de-ethaniser the ethylene, eventually hydrogen when used, is produced overhead and recycled back to the metathesis reactor. The bottom product is further separated in a de-propaniser where the overhead product is the desired propylene. The bottom product is typically butenes and some heavier olefins. The butenes can be recycled back to the metathesis reactor for further reaction.

Figure 2:
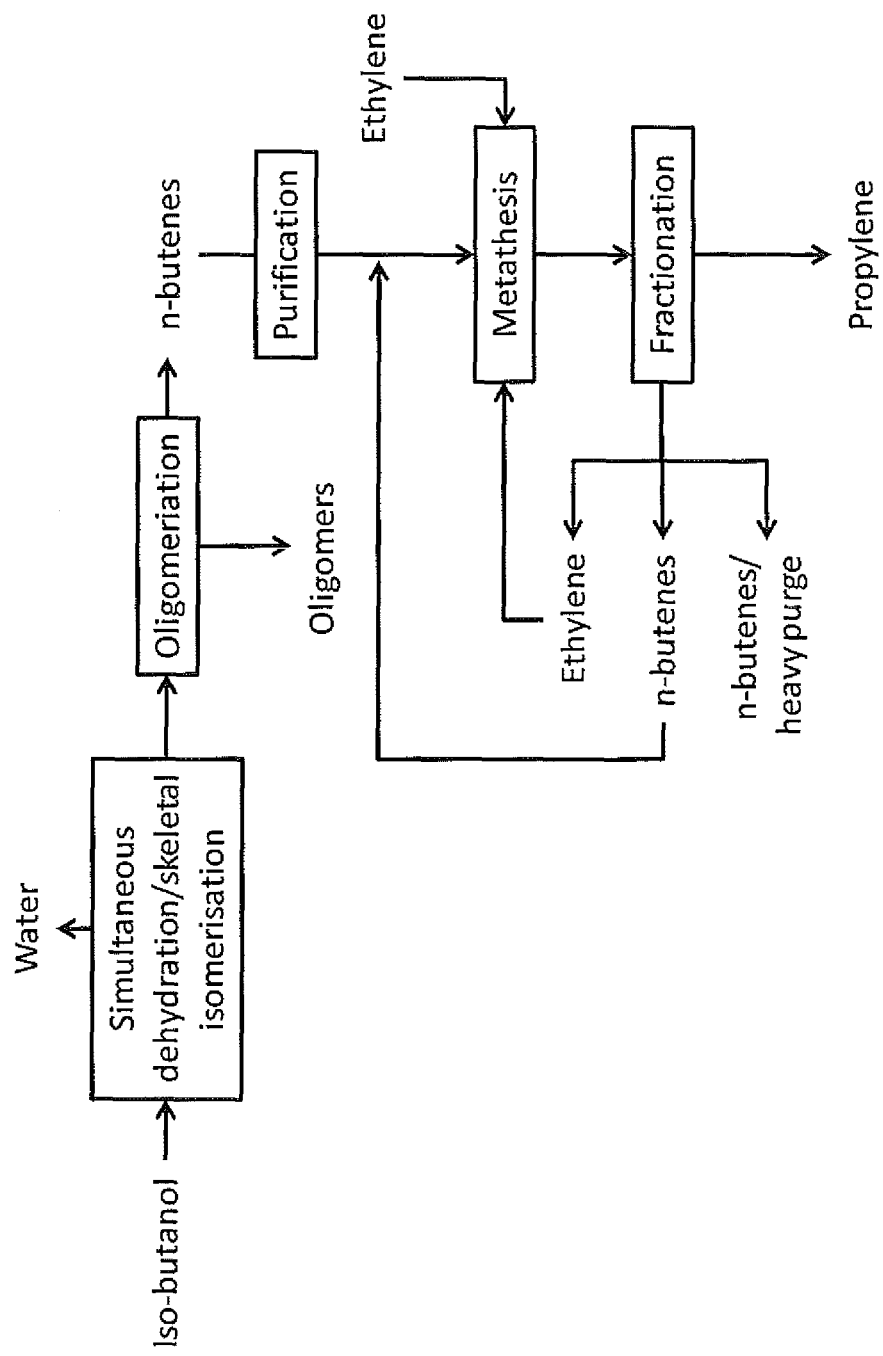
FIG. 2 depicts oligomerisation implementation to remove iso-butene.

FIG. 2 shows the process enchainment with oligomerisation implementation to remove iso-butene. After the simultaneous dehydration/skeletal isomerisation the water product is separated and the mixture of butenes, eventually containing some heavies is oligomerised. The oligomerisation effluent contains oligomers, not-reacted n-butenes and minor amounts of not-converted iso-butene. The substantially not-reacted n-butenes are purified and send to the metathesis reactor alone or mixed with ethylene. The effluent of the metathesis reactor is fractionated: ethylene is recycled back to the metathesis reactor; the remaining n-butenes can also be recycled partially while a purge of butenes and heavies leaves the recycle loop and propylene is obtained as desired product.

Figure 3:
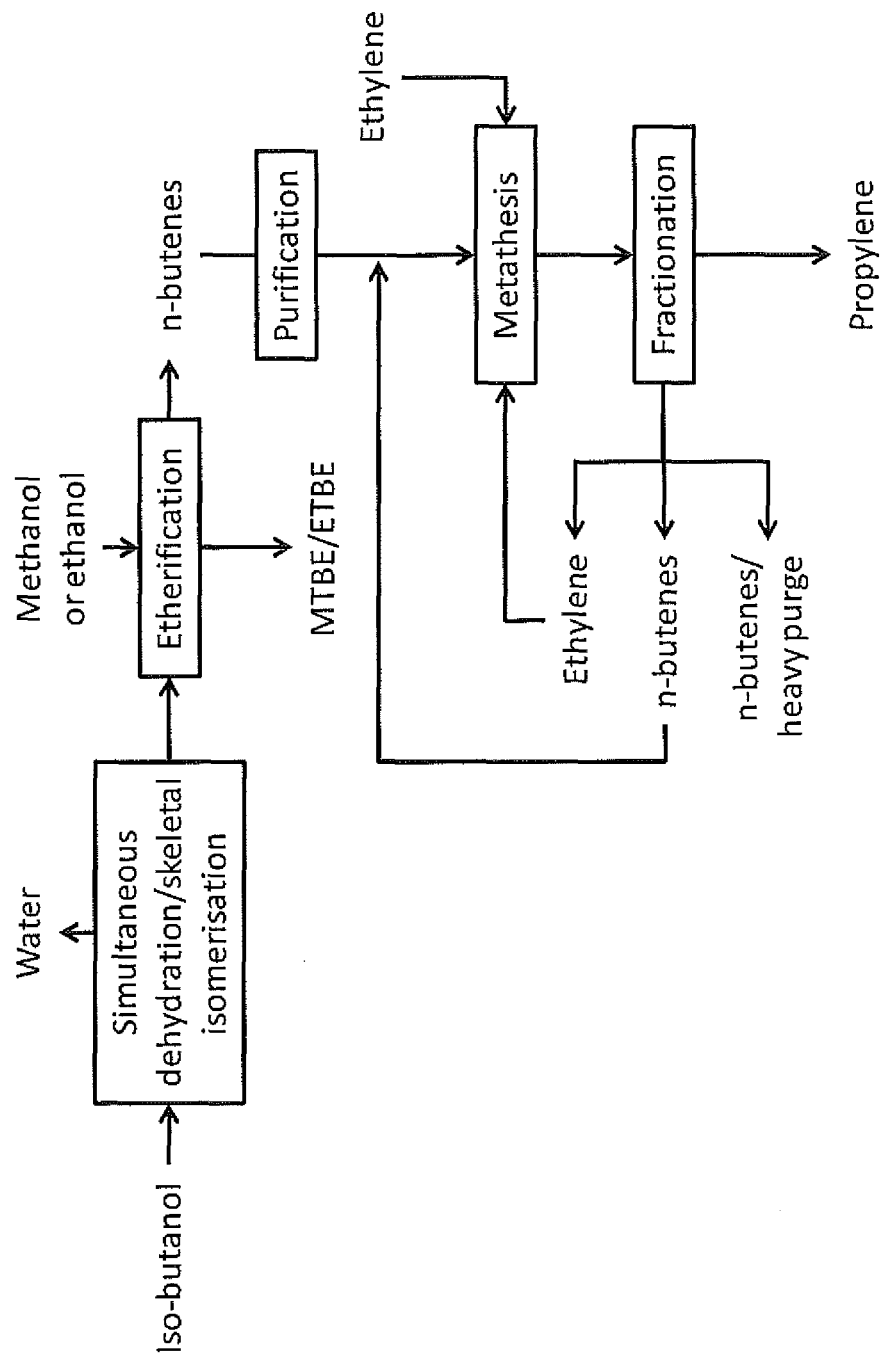
FIG. 3 depicts etherification implementation to remove iso-butene.

FIG. 3 shows the process enchainment with etherification implementation to remove iso-butene. After the simultaneous dehydration/skeletal isomerisation the water product is separated and the mixture of butenes, eventually containing some heavies is etherified by mixing with methanol or ethanol. The etherification effluent contains ethers, not-reacted n-butenes and minor amounts of not-converted iso-butene. The substantially not-reacted n-butenes are purified and send to the metathesis reactor alone or mixed with ethylene. The effluent of the metathesis reactor is fractionated: ethylene is recycled back to the metathesis reactor; the remaining n-butenes can also be recycled partially while a purge of butenes and heavies leaves the recycle loop and propylene is obtained as desired product.

Figure 4:
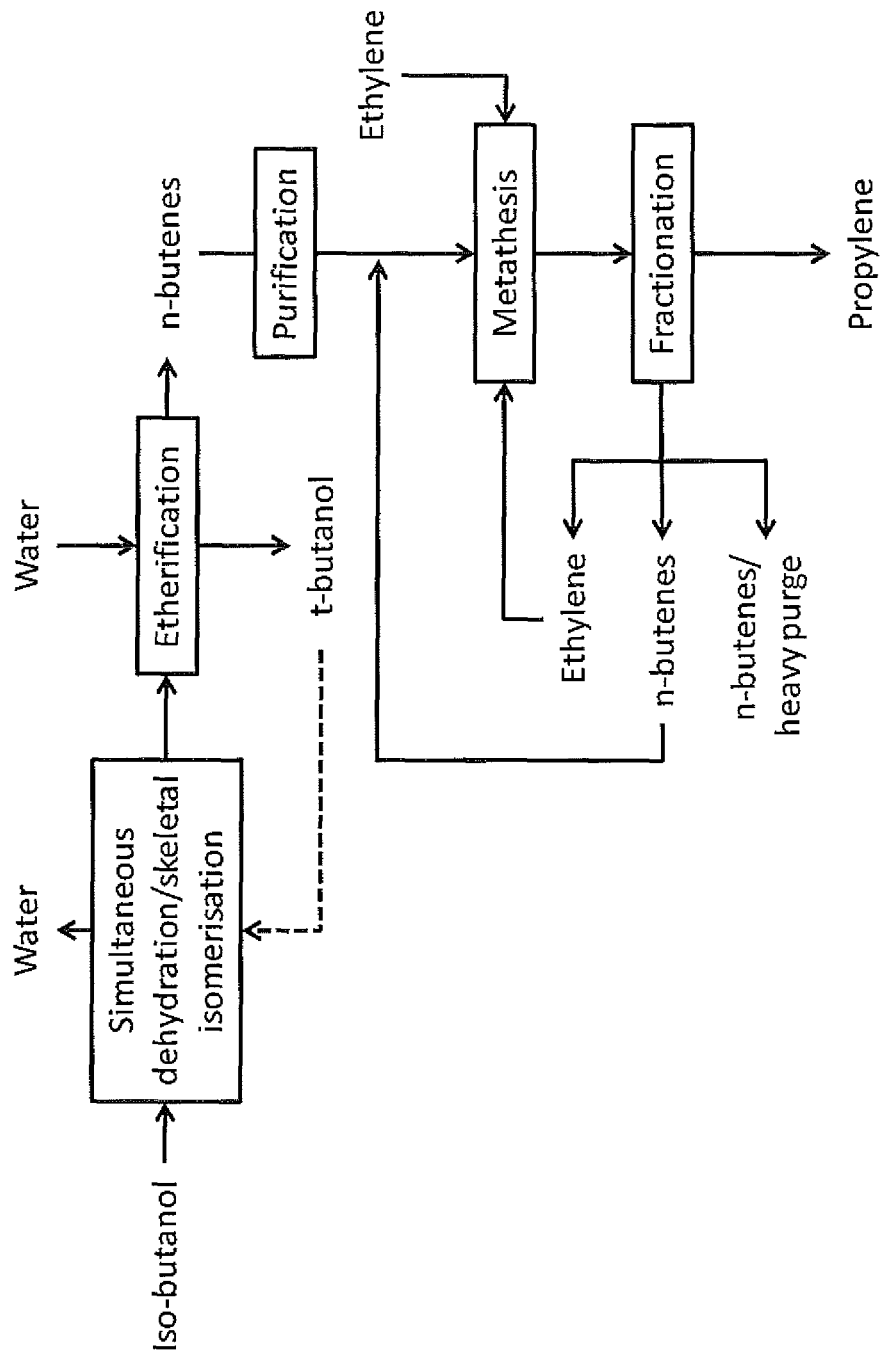
FIG. 4 depicts hydration implementation to remove iso-butene.

FIG. 4 shows the process enchainment with hydration implementation to remove iso-butene. After the simultaneous dehydration/skeletal isomerisation the water product is eventually separated and the mixture of butenes, eventually containing some heavies is hydrated by addition of water. The hydration effluent contains t-butanol, not-reacted n-butenes and minor amounts of not-converted iso-butene. The substantially not-reacted n-butenes are purified and send to the metathesis reactor alone or mixed with ethylene. The effluent of the metathesis reactor is fractionated: ethylene is recycled back to the metathesis reactor; the remaining n-butenes can also be recycled partially while a purge of butenes and heavies leaves the recycle loop and propylene is obtained as desired product. The t-butanol can eventually be recycled back to the simultaneous dehydration/skeletal isomerisation reactor section where it will be simultaneously be dehydration and skeletal isomerised.

Figure 5:
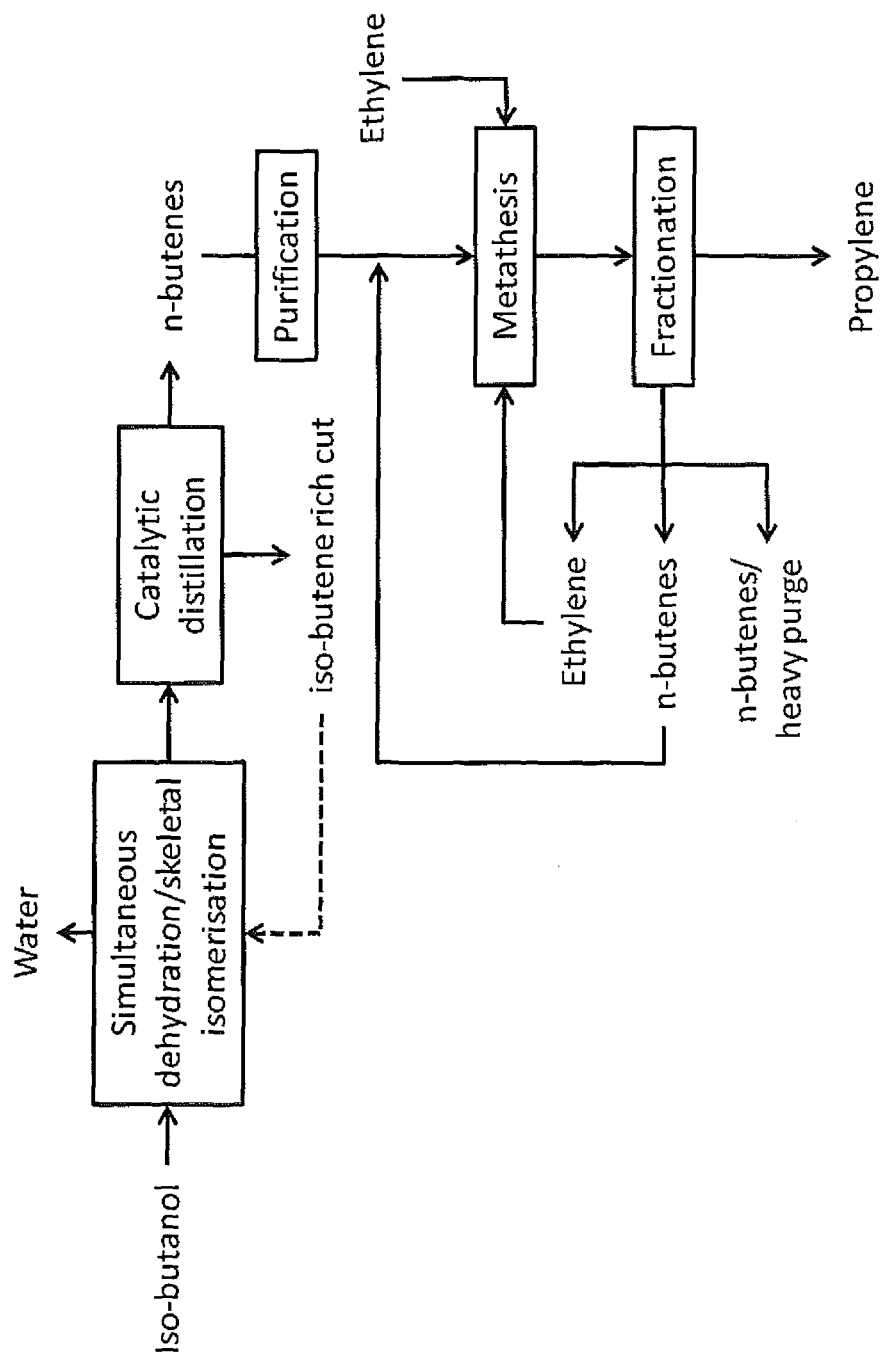
FIG. 5 depicts catalytic distillation implementation to remove iso-butene.

FIG. 5 shows the process enchainment with catalytic distillation implementation to remove iso-butene. After the simultaneous dehydration/skeletal isomerisation the water product is separated and the mixture of butenes, eventually containing some heavies is distilled in a catalytic distillation. The catalytic distillation overhead is a rich iso-butene stream and the bottom product is a rich 2-butenes stream. The 2-butenes stream are purified and send to the metathesis reactor alone or mixed with ethylene. The effluent of the metathesis reactor is fractionated: ethylene is recycled back to the metathesis reactor; the remaining n-butenes can also be recycled partially while a purge of butenes and heavies leaves the recycle loop and propylene is obtained as desired product. The rich iso-butene overhead stream can eventually be recycled back to the simultaneous dehydration/skeletal isomerisation reactor section where it will be further converted into n-butenes.

EXAMPLES

Experimental

The stainless-steel reactor tube has an internal diameter of 10 mm. 10 ml of catalyst, as pellets of 35-45 mesh, is loaded in the tubular reactor. The void spaces before and after the catalyst are filled with SiC granulates of 2 mm. The temperature profile is monitored with the aid of a thermocouple well placed inside the reactor. The reactor temperature is increased at a rate of 60° C./h to 550° C. under air, kept 2 hours at 550° C. and then purged by nitrogen. The nitrogen is then replaced by the feed at the indicated operating conditions.

The catalytic tests are performed down-flow, at 1.5 and 2.0 bara, in a temperature range of 280-380° C. and with a weight hour space velocity (WHSV) varying from 7 to 21 $h^{-1}$.

Analysis of the products is performed by using an on-line gas chromatography.

Example 1

According to the Invention

The catalyst used here is a crystalline silicate of the FER structure. The H-FER has a Si/Al of 33 under powder form. The catalyst is calcinated with air at 550° C. during 4 hours before formulation in pellets of 35-45 mesh.

An isobutanol/water mixture having the 95/5 wt % composition has been processed on the catalyst under 2 bara, at temperatures between 350 and 375° C., and with an isobutanol space velocity from 7 to 21 $h^{-1}$.

In this set of operating conditions, isobutanol conversion is almost complete, with a butenes selectivity of over 95% wt, and an iso-butene selectivity of around 41-43%. Low amounts of $C_4^+$ compounds are formed.

| FEED | iButOH/H2O (95/5)% wt | | | | |
|---|---|---|---|---|---|
| P (bara) | 2 | 2 | 2 | 2 | 2 |
| T (° C.) | 350.0 | 350.0 | 350.0 | 375.0 | 375.0 |
| WHSV (H-1) | 7.3 | 12.6 | 21.0 | 21.0 | 12.6 |
| conversion (% wt CH2) | 100.0 | 99.4 | 89.7 | 99.8 | 99.2 |
| Oxygenates on C-basis (% wt CH2) - average | | | | | |
| Ether | 0.0 | 0.0 | 0.0 | 0.0 | 0.0 |
| Other alcohol | 0.1 | 0.1 | 0.2 | 0.1 | 0.1 |
| Aldehyde + Ketone | 0.1 | 0.1 | 0.1 | 0.1 | 0.1 |
| Yield on C-basis (% wt CH2) - average | | | | | |
| Paraffins | 1.0 | 0.4 | 0.2 | 0.4 | 0.4 |
| C2= | 0.8 | 0.5 | 0.3 | 0.7 | 0.4 |
| C3= | 0.2 | 0.1 | 0.0 | 0.1 | 0.1 |
| C4= | 95.9 | 97.4 | 88.7 | 97.8 | 97.5 |
| C5+ olef | 1.4 | 0.6 | 0.3 | 0.5 | 0.5 |
| Dienes | 0.4 | 0.2 | 0.0 | 0.1 | 0.1 |
| Aromatics | 0.1 | 0.0 | 0.0 | 0.0 | 0.0 |
| Unknown | 0.1 | 0.0 | 0.0 | 0.0 | 0.0 |
| Selectivity on C-basis (% wt CH2) - average | | | | | |
| Paraffins | 1.0 | 0.4 | 0.2 | 0.4 | 0.4 |
| C2= | 0.8 | 0.5 | 0.3 | 0.7 | 0.4 |
| C3= | 0.2 | 0.1 | 0.0 | 0.1 | 0.1 |
| C4= | 95.9 | 98.0 | 98.8 | 97.9 | 98.3 |
| C5+ olef | 1.4 | 0.6 | 0.3 | 0.5 | 0.5 |
| Dienes | 0.4 | 0.2 | 0.0 | 0.1 | 0.1 |
| Aromatics | 0.1 | 0.0 | 0.0 | 0.0 | 0.0 |
| Unknown | 0.1 | 0.0 | 0.0 | 0.0 | 0.0 |
| C4= distribution (% wt CH2) | | | | | |
| i-C4= | 43.4 | 42.2 | 42.4 | 42.2 | 41.6 |
| n-C4= | 56.6 | 57.8 | 57.6 | 57.8 | 58.4 |
| t-2-C4= | 27.0 | 27.7 | 27.9 | 27.0 | 28.0 |
| c-2-C4- | 18.4 | 18.7 | 18.6 | 18.7 | 18.9 |
| 1-C4= | 11.2 | 11.4 | 11.1 | 12.1 | 11.5 |

Comparative Example 2

The catalyst is cylinder-shaped gamma-alumina from Sasol® formulated. The catalyst has a specific surface are of 182 $m^2$/g and a porous volume of 0.481 ml/g. The impurities present on the alumina in small amount are summarized below:

0.25% wt Si, 0.02% wt P, 0.02% wt fe, 29 ppm Na.

An isobutanol/water mixture having the 95/5 wt % composition has been processed on the catalyst under 2 bara, at temperatures between 350 and 380° C., and with an isobutanol space velocity from 7 to 12 $h^{-1}$.

In this set of operating conditions, isobutanol conversion is almost complete, with a butenes selectivity of over 98% wt, and an iso-butene selectivity of around 90-94%. Thus very low amounts of n-butenes are produced over this catalyst. Low amounts of $C_5^+$ compounds are formed.

| FEED | i-ButOH/H2O (95/5)% wt | | | |
|---|---|---|---|---|
| P (bara) | 2 | 2 | 2 | 2 |
| T (° C.) | 380.0 | 350.0 | 350.0 | 325.0 |

-continued

| FEED | i-ButOH/H2O (95/5)% wt | | | |
|---|---|---|---|---|
| WHSV (H-1) | 12.4 | 7.4 | 12.4 | 7.4 |
| Conversion (% wt CH2) | 99.98 | 99.96 | 99.93 | 99.85 |
| Oxygenates (% wt CH2) - average | | | | |
| Other Oxygenates | 0.0 | 0.0 | 0.0 | 0.0 |
| Other alcohol | 0.0 | 0.1 | 0.1 | 0.1 |
| Selectivity on C-basis (% wt CH2) - average | | | | |
| Paraffins | 0.3 | 0.3 | 0.1 | 0.3 |
| C2= | 0.3 | 0.2 | 0.2 | 0.1 |
| C3= | 0.2 | 0.1 | 0.0 | 0.0 |
| C4= | 98.2 | 98.6 | 99.1 | 98.6 |
| C5+ olef | 0.7 | 0.5 | 0.1 | 0.3 |
| Dienes | 0.1 | 0.0 | 0.0 | 0.1 |
| Aromatics | 0.0 | 0.0 | 0.0 | 0.0 |
| Unknown | 0.1 | 0.1 | 0.3 | 0.4 |
| C4= distribution (% wt) | | | | |
| iC4= | 90.2 | 92.5 | 92.7 | 94.0 |
| t-2-C4= | 3.0 | 1.8 | 1.4 | 1.2 |
| c-2-C4- | 3.9 | 3.2 | 3.3 | 2.7 |
| 1-C4= | 2.9 | 2.5 | 2.6 | 2.1 |
| n-C4= | 9.8 | 7.5 | 7.3 | 6.0 |

Example 3

According to the Invention

The catalyst is a phosphorous modified zeolite (P-ZSM5), prepared according to the following recipe. A sample of zeolite ZSM-5 (Si/Al=13) in H-form was steamed at 550° C. for 6 h in 100% $H_2O$. The steamed solid was subjected to a contact with an aqueous solution of $H_3PO_4$ (85% wt) for 2 h under reflux condition (4 ml/1 g zeolite). Then 69.9 g of CaCO3 was introduced by maintaining a pH of 2.52. Then the solution was dried by evaporation for 3 days at 80° C. 750 g of the dried sample was extruded with 401.5 g of Bindzil and 0.01 wt % of extrusion additives. The extruded solid was dried at 110° C. for 16 h and calcinated at 600° C. for 10 h.

An isobutanol/water mixture having the 95/5 wt % composition has been processed on the catalyst under 1.5 bara, at temperatures between 280 and 350° C., and with an isobutanol space velocity of about 7 $h^{-1}$.

In this set of operating conditions, isobutanol conversion is almost complete, with a butenes selectivity of over 90% wt, and an iso-butene selectivity of about 66-67%. Thus, nearly 90% or more butenes are produced of which a significant amount are skeletal isomerised into n-butenes. The heavies production is limited to 10% or less.

| FEED: i-ButOH/H2O (95/5)% wt | | |
|---|---|---|
| P (bara) | 1.5 | 1.5 |
| T (° C.) | 300 | 280 |
| WHSV (H-1) | 7.4 | 7.4 |
| Conversion (% wt CH2) | 100.0 | 83.5 |
| Oxygenates (% wt CH2) - Average | | |
| Other alcohols | 0.01 | 0.00 |
| Other Oxygenates | 0.03 | 0.08 |
| Selectivity on C-basis (% wt CH2) - Average | | |
| Paraffins C1-C4 | 0.1 | 0.1 |
| C2= | 0.0 | 0.0 |
| C3= | 0.5 | 0.3 |
| C4= | 89.9 | 93.9 |
| i-Butene | 60.3 | 61.9 |
| 1-Butene | 5.0 | 6.1 |
| 2-Butene | 24.6 | 26.0 |
| C5+ olef | 4.8 | 2.7 |
| C5+ paraf | 1.9 | 1.1 |
| Dienes | 0.5 | 0.4 |
| Aromatics | 0.5 | 0.2 |
| Unknown | 1.6 | 1.1 |
| C4= distribution - Average | | |
| i-Butene | 67.1 | 65.9 |
| n-butenes | 32.9 | 34.1 |
| 1-Butene | 5.5 | 6.5 |
| 2-Butene | 27.4 | 27.7 |

What is claimed:

1. A process for the production of propylene in which in a first step isobutanol is subjected to a simultaneous dehydration and skeletal isomerisation to make corresponding olefins, having the same number of carbons and comprising a mixture of n-butenes and iso-butene and in a second step n-butenes are subjected to methathesis, said process comprising:
    a) introducing in a dehydration and isomerization reactor a stream (A) comprising isobutanol, wherein the isobutanol is present in the stream (A) in an amount ranging from 30 to 100 weight percent based on a total weight of the stream (A),
    b) contacting said stream (A) with a dehydration and isomerization catalyst in said dehydration and isomerization reactor at conditions effective to dehydrate at least a portion of the isobutanol and skeletal isomerase an iso-butyl moiety of at least a portion of the isobutanol to make a mixture of n-butenes and iso-butene, wherein the dehydration and isomerization catalyst is a crystalline silicate; a dealuminated crystalline silicate; a phosphorus modified crystalline silicate; a silicoalumina-phosphate molecular sieve; or a silicated, zirconated, titanated, or fluorinated alumina,
    c) recovering from said dehydration and isomerization reactor a stream (B) comprising the mixture of n-butenes and iso-butene,
    d) fractionating said mixture of n-butenes and iso-butene to produce an n-butenes stream (N) and to remove at least part of the isobutene,
    e) sending the n-butenes stream (N) to a methathesis reactor and contacting the n-butenes stream (N) with a methathesis catalyst in said methathesis reactor, at conditions effective to produce propylene,
    f) recovering from said methathesis reactor a stream (P) comprising propylene, unreacted n-butenes, and heavies,
    g) fractionating the stream (P) to recover propylene.

2. The process according to claim 1 wherein the WHSV of the isobutanol in the dehydration and isomerization reactor is at least 1 $h^{-1}$.

3. The process according to claim 1 wherein the temperature in the dehydration and isomerization reactor ranges from 200° C. to 600° C.

4. The process according to claim 1, wherein the dehydration and isomerization catalyst for the simultaneous dehydration and skeletal isomerisation is a dealuminated crystalline silicate of the group FER, MWW, EUO, MFS, ZSM-48, MTT, MFI, MEL or TON having Si/Al higher than 10.

5. The process according to claim 1 wherein the dehydration and isomerization catalyst for the simultaneous dehydration and skeletal isomerisation is a crystalline silicate of the group FER, MWW, EUO, MFS, ZSM-48, MTT, MFI, MEL or TON having Si/Al higher than 10.

6. The process according to claim 1 wherein the n-butenes stream (N) of step d) comprises less than 10 w % of iso-butene.

7. The process according to claim 1 wherein in the fractionation of step d) iso-butene is removed by selective oligomerisation of iso-butene.

8. The process according to claim 1 wherein in the fractionation of step d) iso-butene is removed by selective etherification with methanol or ethanol.

9. The process according to claim 1 wherein in the fractionation of step d) iso-butene is removed by selective hydration into t-butanol.

10. The process according to claim 9 wherein said t-butanol is recycled to the dehydration and isomerization reactor of step b).

11. The process according to claim 1 wherein the metathesis is carried out as autometathesis with only butenes as feedstock.

12. The process according to claim 1 wherein the n-butenes stream (N) recovered at step d) is sent to an isomerisation unit to produce a n-butenes stream having a reduced 1-butene content and an enhanced 2-butene content, then said stream is sent to the metathesis reactor.

13. The process according to claim 1 wherein the fractionation of step d) is made by a catalytic distillation column wherein part of the 1-butene is isomerised to 2-butene, iso-butene is recovered as overhead and 2-butene is recovered in the bottoms of said column.

14. The process according to claim 13 wherein iso-butene is recycled to the dehydration and isomerization reactor of step b).

15. The process according to claim 14 wherein the metathesis is carried out by adding ethylene to the butenes.

16. The process according to claim 1 wherein the pressure of the dehydration and isomerization reactor ranges from 0.5 to 10 bars absolute.

17. The process according to claim 1, wherein the dehydration and isomerization catalyst for the simultaneous dehydration and skeletal isomerisation is a phosphorus modified crystalline silicate of the group FER, MWW, EUO, MFS, ZSM-48, MTT, MFI, MEL or TON having Si/Al higher than 10.

18. The process according to claim 1, wherein the dehydration and isomerization catalyst for the simultaneous dehydration and skeletal isomerisation is a silicoaluminaphosphate molecular sieve of the group AEL.

19. The process according to claim 1 wherein the metathesis catalyst is a metallic oxide dispersed on a carrier, wherein the metallic oxide is selected from molybdenum, tungsten or rhenium, and wherein the carrier is selected from alumina or silica containing carrier.

20. The process according to claim 1 wherein in the course of methathesis hydrogen is added to the metathesis reactor in an amount ranging between 0.1 and 10 vol % of the n-butenes stream (N).

21. The process according to claim 1 wherein among the butenes produced at step c) the proportion of n-butenes is above 20%.

22. The process according to claim 21 wherein among the butenes produced at step c) the proportion of n-butenes is above 30%.

23. The process according to claim 22 wherein among the butenes produced at step c) the proportion of n-butenes is above 40%.

24. The process according to claim 23 wherein among the butenes produced at step c) the proportion of n-butenes is above 50%.

25. A process comprising:
contacting isobutanol with a dehydration and isomerization catalyst in a dehydration and isomerization reactor at conditions effective to dehydrate at least a portion of the isobutanol and to skeletal isomerase an iso-butyl moiety of at least a portion of the isobutanol to make a mixture of n-butenes and iso-butene, wherein the isobutanol is present in the stream (A) in an amount ranging from 30 to 100 weight percent based on a total weight of the stream (A), and wherein the dehydration and isomerization catalyst is a crystalline silicate; a dealuminated crystalline silicate; a phosphorus modified crystalline silicate; a silicoaluminaphosphate molecular sieve; or a silicated, zirconated, titanated, or fluorinated alumina;
recovering from said dehydration and isomerization reactor the mixture of n-butenes and iso-butene;
fractionating the mixture to produce an n-butenes stream (N) and to remove at least part of the isobutene;
contacting the n-butenes stream (N) with a metathesis catalyst in a metathesis reactor at conditions effective to produce propylene;
recovering from the methathesis reactor a stream (P) comprising propylene; and
fractionating the stream (P) to recover propylene.

26. The process according to claim 1, wherein the dehydration and isomerization catalyst for the simultaneous dehydration and skeletal isomerisation is a silicated, zirconated or titanated or fluorinated alumina.

27. The process according to claim 1, wherein the dehydration and isomerization catalyst for the simultaneous dehydration and skeletal isomerisation is a crystalline silicate of the group FER or MFI having Si/Al higher than 10, a dealuminated crystalline silicate of the group FER or MFI having Si/Al higher than 10, or a phosphorus modified crystalline silicate of the group FER or MFI having Si/Al higher than 10.

28. The process according to claim 1, wherein a ratio of isobutanol to all other $C_4$ alcohols in the stream (A) is 42% or above.

* * * * *